(12) United States Patent
Sanchez et al.

(10) Patent No.: US 8,374,696 B2
(45) Date of Patent: Feb. 12, 2013

(54) CLOSED-LOOP MICRO-CONTROL SYSTEM FOR PREDICTING AND PREVENTING EPILEPTIC SEIZURES

(75) Inventors: Justin C. Sanchez, Newberry, FL (US); Paul R. Carney, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 690 days.

(21) Appl. No.: 11/520,222

(22) Filed: Sep. 13, 2006

(65) Prior Publication Data

US 2007/0067003 A1 Mar. 22, 2007

Related U.S. Application Data

(60) Provisional application No. 60/716,863, filed on Sep. 14, 2005.

(51) Int. Cl.
*A61N 1/36* (2006.01)
(52) U.S. Cl. .......................................................... 607/45
(58) Field of Classification Search ...................... 607/45
See application file for complete search history.

(56) References Cited

U.S. PATENT DOCUMENTS

| | | | | |
|---|---|---|---|---|
| 4,408,616 A * | 10/1983 | Duffy et al. | .................... | 600/544 |
| 6,810,285 B2 * | 10/2004 | Pless et al. | .................... | 600/544 |
| 7,277,758 B2 * | 10/2007 | DiLorenzo | ...................... | 607/45 |
| 7,353,065 B2 * | 4/2008 | Morrell | ........................... | 607/45 |

OTHER PUBLICATIONS

Vonck et al. Long-term Amygdalohippocampal Stimulation for Refractory Temporal Lobe Epilepsy. Ann. Neurol. (2002) 52:556-565.*

Fried, et al., "Cerebral microdialysis combined with single-neuron and electroencephalographic recording in neurosurgical patients", J. Neurosurg 91:697-705 (1999).

Tropp Sneider, et al., "Differential Behavioral State-Dependence in the Burst Properties of CA3 and CA1 Neurons", 141 Neuroscience 1665-1677 (2006).

Chaovalitwongse, et al., "Performance of a seizure warning algorithm based on the dynamics of intracranial EEG", 64 Epilepsy Research 93-113 (2005).

Sanchez, et al., "Evolving into epilepsy: Multiscale electrophysiological analysis and imaging in an animal model", 198 Experimental Neurology 31-47 (2006).

Carney, et al., "Quantitative Analysis of EEG in the Rat Limbic Epilepsy Model", Neurology 62 Apr. 2004 (Suppl 5).

(Continued)

*Primary Examiner* — Carl H Layno
*Assistant Examiner* — Jeremiah Kimball
(74) *Attorney, Agent, or Firm* — Edwards Wildman Palmer LLP; Peter F. Corless; Brian R. Landry

(57) ABSTRACT

The invention provides a micro-control neuroprosthetic device and methods for predicting and controlling epileptic neuronal activity. The device includes a detection system that detects and collects electrophysiological information comprising action potentials from single neurons and ensembles of neurons in a neural structure such as an epileptogenic region of the brain in a subject. An analysis system included in the neuroprosthetic device evaluates the electrophysiological information and performs a real-time extraction of neuron firing features from which the system determines when stimulus intervention is required. The neuroprosthetic device further comprises a stimulation intervention system that provides stimulus output signals having a desired stimulation frequency and stimulation intensity directly to the neural structure in which abnormal neuronal activity is detected. The analysis system further analyzes collected electrophysiological information during or following stimulus intervention to assess the effects of the stimulation intervention and to provide outputs to maintain or modify the stimulation intervention.

17 Claims, 15 Drawing Sheets

OTHER PUBLICATIONS

Iasemidis, et al., "Long-term prospective on-line real-time seizure prediction", 116 Clinical Neurophysiology 532-544 (2005).

Carney, et al., "State-Specific Nonlinear Neurodynamic Features in an Animal Model of Generalized Epilepsy", Epilepsia, vol. 43, Suppl. 7 (2002).

Iasemidis, et al., "Adaptive Epileptic Seizure Prediction System", 50(5) IEEE Transactions on Biomedical Engineering (May 2003).

Sanchez, et al., "Identifying the Seizure Onset Zone Using Amplitude Modulated Slow Potentials, Gamma, Fast Gamma, and Neural Ensemble Activity", Epilepsia, vol. 47, S4, 2006.

* cited by examiner ions of normal brain function. As a chronic condition, epilepsy affects about 1% of the population in the United States. This prevalence will increase substantially in the near future largely due to the rapidly expanding number of elderly Americans, in whom the incidence of epilepsy is the highest. Uncontrolled epilepsy poses a significant burden to society due to associated healthcare costs and chronic under-unemployment of otherwise physically and mentally competent individuals.

CLOSED-LOOP MICRO-CONTROL SYSTEM FOR PREDICTING AND PREVENTING EPILEPTIC SEIZURES

CROSS-REFERENCE TO RELATED APPLICATIONS

The present application claims priority under 35 U.S.C. 119(e) to U.S. Provisional Application No. 60/716,863 entitled Closed-Loop Micro-Control System for Predicting and Preventing Epileptic Seizures, filed Sep. 14, 2005, the disclosure of which is hereby incorporated by reference in its entirety.

STATEMENT OF U.S. GOVERNMENT INTEREST

Funding for the present invention was provided in part by the Government of the United States under Grant Nos.: R01-NS050582-01A1, R01-EB004752-01, and R01-EB002089-03 from the National Institutes of Health and National Science Foundation (NSF/NIH (NBIB)). Accordingly, the Government of the United States has certain rights in and to the invention.

FIELD OF THE INVENTION

The invention generally relates to the prediction and intervention of seizures in subjects with epilepsy and related disorders. More specifically, it relates to devices and methods for seizure prediction and intervention by electrical stimulation therapy to the brain.

BACKGROUND

The epilepsies are a family of neurological disorders characterized by seizures, which are transient, recurrent perturbations of normal brain function. As a chronic condition, epilepsy affects about 1% of the population in the United States. This prevalence will increase substantially in the near future largely due to the rapidly expanding number of elderly Americans, in whom the incidence of epilepsy is the highest. Uncontrolled epilepsy poses a significant burden to society due to associated healthcare costs and chronic under-unemployment of otherwise physically and mentally competent individuals.

Anti-epileptic drug (AED) treatment is the standard therapy for epilepsy. Unfortunately, AEDs in current therapeutic use display significant side effect profiles. Additionally, about one third of all patients remain unresponsive to currently available medications. The need for more effective treatments for phamacoresistant epilepsy was among the driving forces behind a recent White House-initiated 'Curing Epilepsy: Focus on the Future' ('Cure') Conference (March, 2000), which emphasized specific research directions and benchmarks for the development of effective and safe treatments for people with epilepsy [3].

At the physiological level, seizure activity involves the transient, simultaneous hypersynchronous activation of a large population of neurons, either in one focal area, or throughout the brain, depending on the type of epilepsy. One of the more common forms of epilepsy in humans that is frequently resistant to current therapy is the mesial temporal lobe epilepsy syndrome, or limbic epilepsy, that originates from limbic structures such as the hippocampus and amygdala [4].

An alternative approach to controlling epilepsy with drugs is through the use of neuroprosthetic devices. For nearly thirty years, epileptologists have been studying macroscopic electroencephalographic (EEG) recordings from the scalp to obtain global and local measures of scalp potentials using a variety of linear, nonlinear, and dynamical computational measures [13-17]. On the surface of the cortex, ECoG grid electrodes have been used in the clinical setting to determine epileptic foci. In this approach, the analysis of the signals is conducted on a gross scale, that is at a system and circuit mechanism level, not at the cellular level [18, 19].

In studies performed in vitro using recent advances in multi-site electrode technology, acute preparations of hippocampal recordings have generated the basic constructs of neuronal firing related to the epileptic condition [20]. In conjunction with in vivo recordings in both humans and animals, "slice physiologists" have performed elegant experiments to infer the normal and bursting responses of single units in excised tissue [21]. It is recognized that such recordings from acute and slice preparations have provided significant contributions to research in the epilepsy field; however they are limited by the loss of network input and output from the rest of the brain (slice), and inability to chronically spontaneously seize, as do human subjects with temporal lobe epilepsy.

Several neuroprosthetic systems to treat epilepsy are presently available. The only existing seizure control system to have received FDA approval is based on electrical stimulation of the vagus nerve. The system is marketed by Cyberonics, Inc. (Houston, Tex.). Another system, developed by Neuropace (Mountain View, Calif.) delivers electrical stimulation to the brain by way of subdural strips upon detection of a electrical signals that occur at the start of a seizure.

Despite these advances, effective neuroprosthetics capable of predicting or warning of impending seizures and delivering timely therapeutic intervention have not been developed. The hallmark of epilepsy is recurrent seizures that are unpredictable and debilitating. Methods of seizure prediction in real-time would have significant impact on patients' lives. Even a few minutes of warning would allow a person experiencing a seizure to stop driving or get out of a risky environment to seek safety. Efforts in this area been limited by a lack of electrophysiologic control parameters that can be used to accurately predict the onset of the epileptic state and to deliver therapeutic feedback to the affected neural structures. In currently available systems, overall patterns of neuronal activity associated with the onset of seizure are detected, and upon such detection, standardized therapy is delivered to the brain in the form of electrical stimulation. The delivered stimulation is of pre-determined strength and duration, regardless of the strength or duration of the seizure. This lack of control results in delivery of an electrical stimulus that may either be insufficient or excessive, both with respect to duration and stimulus strength.

To predict and effectively treat an epileptic seizure, a "closed-loop" system is needed in which sensitive physiological parameters associated with an oncoming epileptic episode are used to detect the preictal state that precedes a seizure. Upon such detection, a stimulus of strength and duration appropriate to control the seizure would be delivered. Development of such devices for seizure prediction and treatment for epilepsy and related disorders would greatly improve the lives of many patients and yield considerable social benefits.

SUMMARY OF THE INVENTION

The invention addresses some of the deficiencies in the art by providing a system and method for epilepsy prediction and seizure prevention based on an implantable neuroprosthetic device that measures action potentials of neurons in the brain. The system provides a method of communicating with, and altering the functions of single neurons or ensembles of neurons that are involved in an abnormal electrophysiological process that is predictive of an epileptic seizure. Upon detection of abnormal firing patterns of neurons, the neuroprosthetic device delivers electrical stimulation therapy in the form of local micro-stimulation to modulate the activity of affected single neurons or ensembles of neurons, thereby delaying or reducing spike wave activity associated with seizures. The device delivers micro-intervention at the level of single neurons or ensembles of neurons involved in the seizure, such as those of limbic structures and associated neural pathways. Utilizing a closed-loop design, the device monitors the effects of the therapy through a continuous feedback process and modifies the duration or strength of the therapeutic stimuli as appropriate.

Accordingly, and in one aspect, the invention provides a micro-control neuroprosthetic device for predicting and controlling epileptic neuronal activity. The device includes a detection system that detects and collects electrophysiological information including action potentials from single neurons and ensembles of neurons in a neural structure. The neural structure is preferably in a region of the brain susceptible to seizure, such as, but not limited to, the limbic system, hippocampus, entorhinal cortex, CA1, CA2, CA3, dentate, or hippocampal commissure.

The device further includes an analysis system that evaluates the detected and collected electrophysiological information and performs a real-time extraction of neuron firing features. From the extracted features, the device determines when electrical stimulus intervention is required.

The device further comprises a stimulation intervention system that provides electrical stimulus output signals having a desired stimulation frequency and stimulation intensity directly to the neural structure being monitored and in which abnormal neuronal activity is detected.

The analysis system further analyzes collected electrophysiological information during and following stimulus intervention, for example to assess the short-term effects of the stimulation intervention and to provide further outputs to either maintain or modify the electrical stimulation intervention.

In some embodiments of the micro-control neuroprosthetic device, the detection system includes a plurality of electrodes forming a multi-site array. The electrode array can further include a switching stage to selectively couple the array to the detector and to the stimulation intervention system. In some preferred embodiments, the electrode array is arranged so as to form a plurality of discrete channels, wherein the switching stage is operated by the stimulation intervention system such that output signals are directed to one or more of the plurality of channels in which it is determined that electrical stimulation intervention is required.

In another aspect, the invention provides a method for controlling epileptic neuronal activity. The method includes the steps of monitoring a neural structure and detecting and collecting electrophysiological information comprising action potentials of single neurons or ensembles of neurons in the neural structure being monitored. The detected and collected electrophysiological information is analyzed and a real-time extraction of neuron firing features is performed. The step of performing a real-time extraction of neuron firing features includes performing at least one analysis selected from, but not limited to, coefficient of variation, spectral analysis, signal integration, signal energy, match filter, hidden Markov modeling, linear predictive modeling, and non-linear predictive modeling (dynamical or feedforward).

From the extraction of firing features, the onset of an epileptic state and of abnormal neural firing is detected. Following such detection, the method includes the step of providing stimulation output signals having a desired stimulation frequency and stimulation intensity to at least a portion of a neural structure being monitored that is responsive to the determining, to control the epileptic neuronal activity.

The method can further comprise collecting electrophysiological information during or following the step of providing stimulation output signals, and analyzing the collected information for example to assess the short-term effects of the stimulation output signals on the onset of the epileptic state or abnormal neural firing.

The method can further include determining from the analyzing if there is increased, decreased or maintenance of neuron/ensemble activity, and maintaining or modifying the stimulation output signals being provided, based on the determination of increased, decreased or maintenance of neuron/ensemble activity.

The method can also comprise providing an electrode array being configured to selectively detect electrophysiological information comprising action potentials, and to output the stimulation output signal. The electrode array being configured is configured so as to create a plurality of channels. Providing stimulation output signals includes providing stimulation output signals having a desired stimulation frequency and stimulation intensity to one or more of the plurality of channels, in which in said one or more channels it is determined that there is onset of an epileptic state or abnormal neuronal firing.

A particularly advantageous feature of the invention is its closed loop control of therapeutic electrical stimulation. Closed-loop control allows for evaluation and adjustment of the stimulus in real-time, i.e., during the pre-seizure state, allowing for delivery of a therapeutic electrical stimulus of appropriate intensity and duration sufficient to prevent or reduce the severity of the seizure.

In contrast to drug therapies, electrical stimulation delivered according to the closed-loop micro-control devices and methods of the invention are believed to offer higher resolution, the advantage of local specificity, and dosage delivery that can be more rapidly varied.

Other aspects and advantages of the invention are discussed below.

4, which is used as a measure of firing irregularity according to an embodiment of the invention.

Figure 5A:
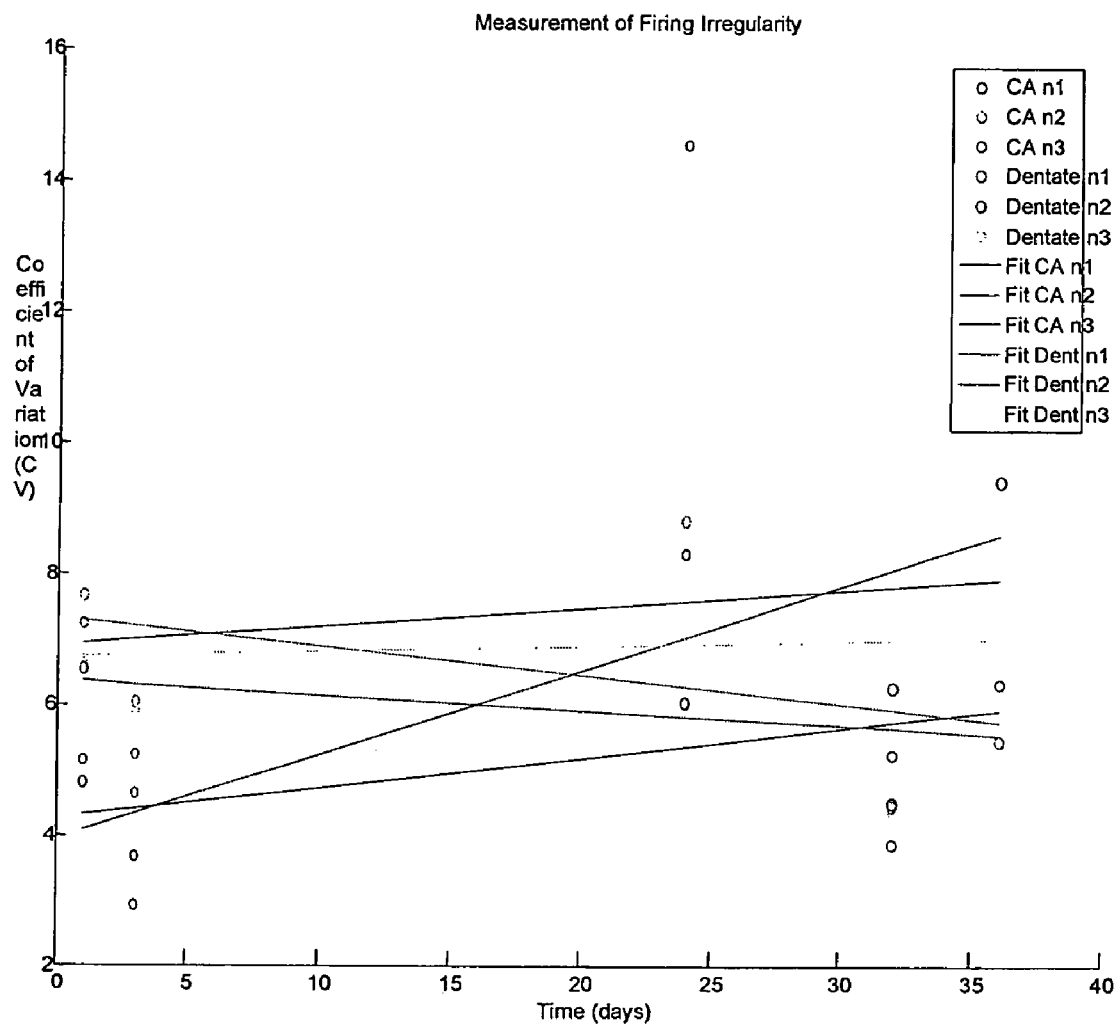
FIG. 5A is a graph illustrating modulation of coefficient of variation as a function of time for the neurons tested in FIG.
Figure 5B:
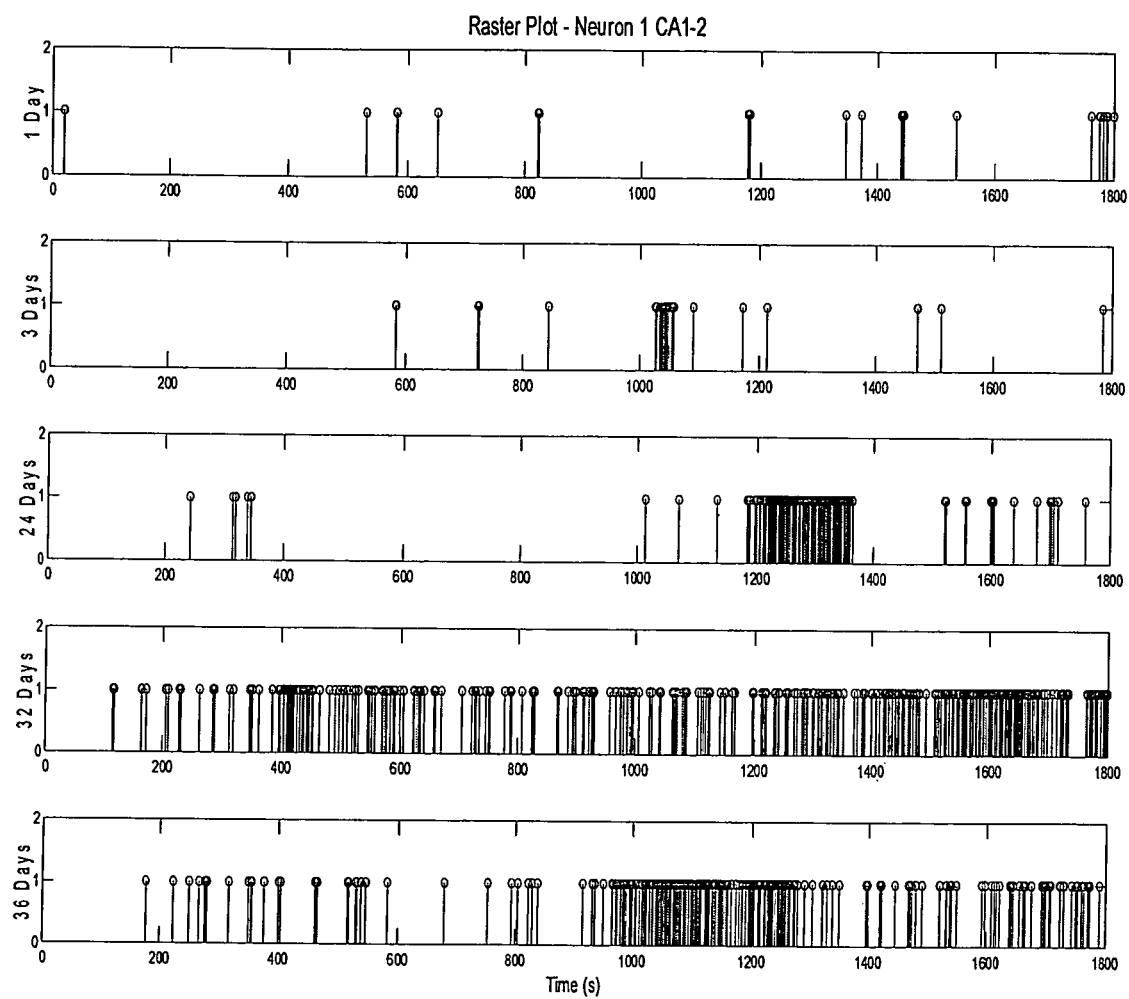

FIG. 5B is a raster plot illustrating coefficient of variation analysis for a single neuron (neuron 1 in CA1) at the indicated time points following stimulation.

Figure 6:
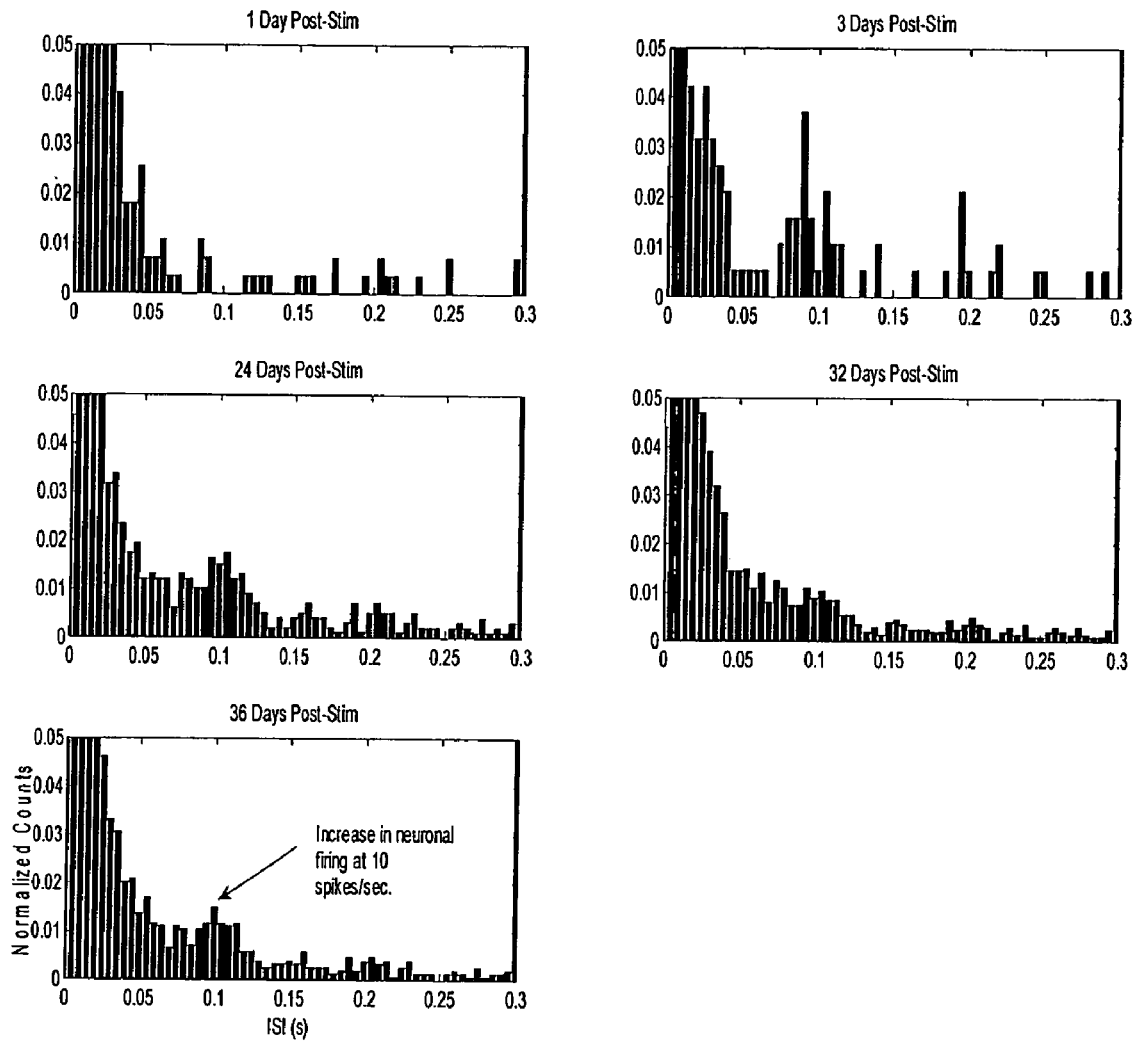

FIG. 6 is a series of interspike interval histograms used for analysis of neuronal firing features according to an embodiment of the invention.

Figure 7:
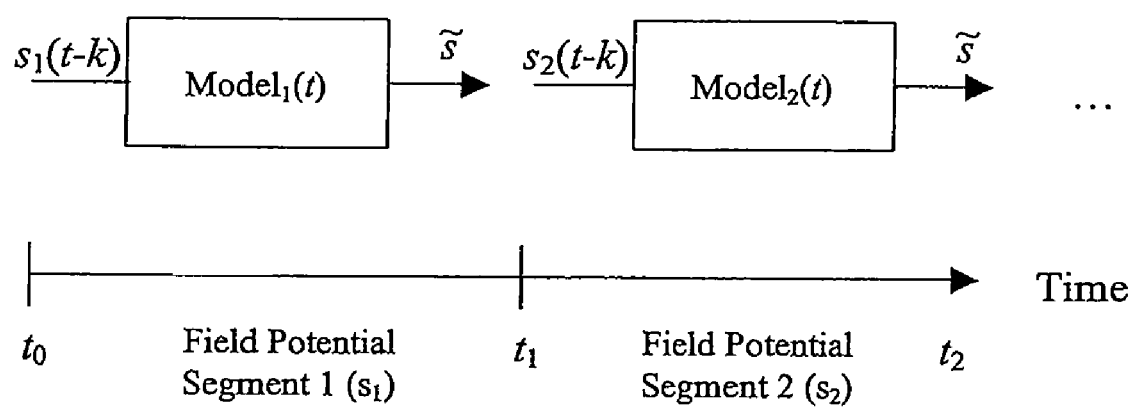

FIG. 7 is a schematic diagram of a linear autoregressive modeling method of signal processing used to analyze local bursts in field potentials generated from ensembles of neurons in the vicinity of an electrode tip, according to an embodiment of the invention.

Figure 8A:
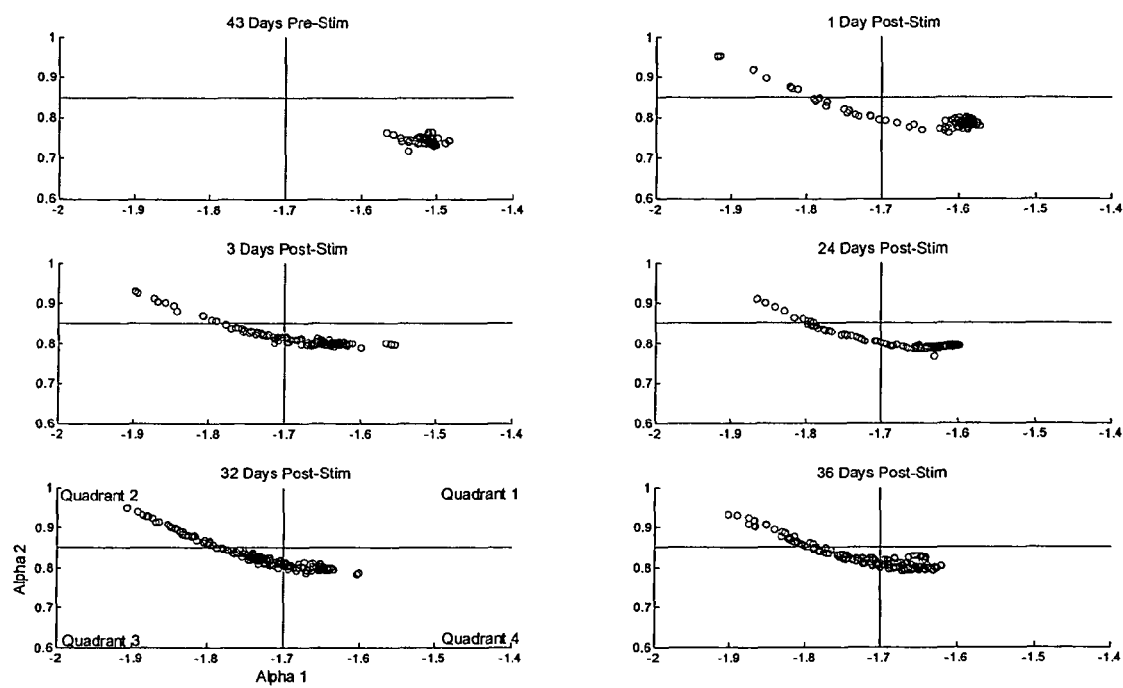

FIG. 8A is a series of graphs illustrating clustering of parameters over time into quadrants designated 1-4 at various times after electrical stimulation in an analytical method according to an embodiment of the invention.

Figure 8B:
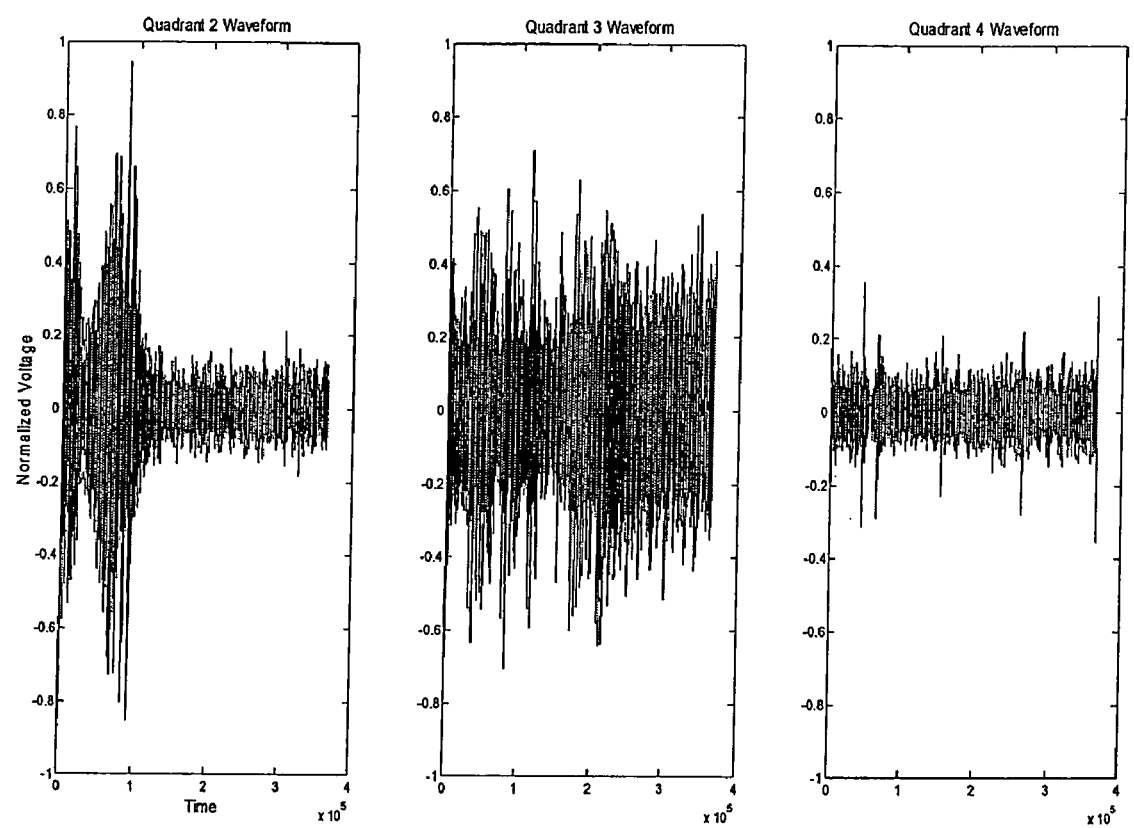

FIG. 8B is three graphs illustrating representative ensemble waveforms from models illustrated in Quadrants 2-4 of FIG. 8A, according to an embodiment of the invention.

Figure 9:
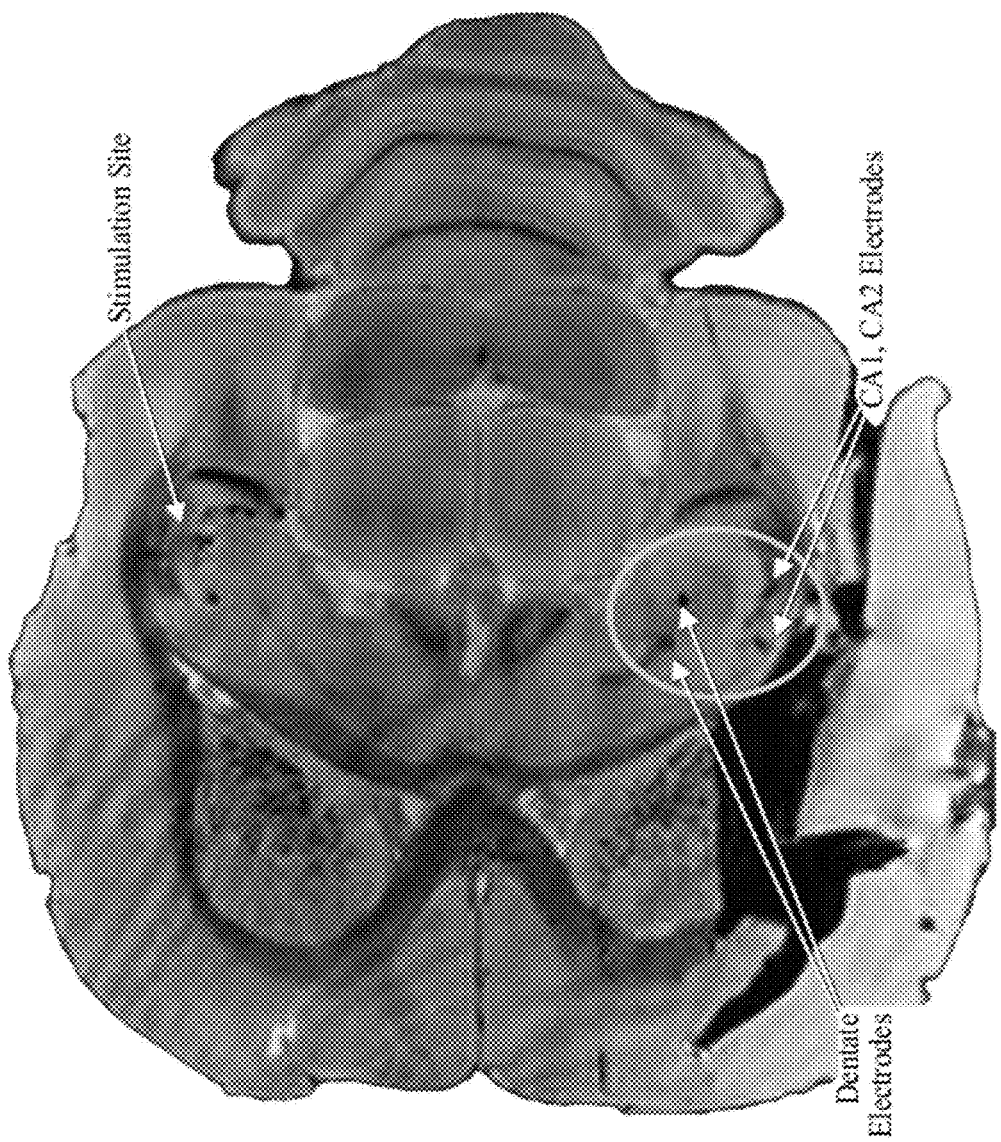

FIG. 9 is a photograph illustrating a representative MR image of a section through the brain of an animal model of spontaneous seizure induced by electrical stimulation of the hippocampus, showing placement of recording electrodes in the CA1, CA2 and dentate regions of the brain.

FIG. 10 is an electrical recording (A) and a graph (B) illustrating firing of an isolated neuron (10A) from an electrode array implanted for 10 in a rat brain and neural response to an intermixing stimulation study (10B).

Figure 11:
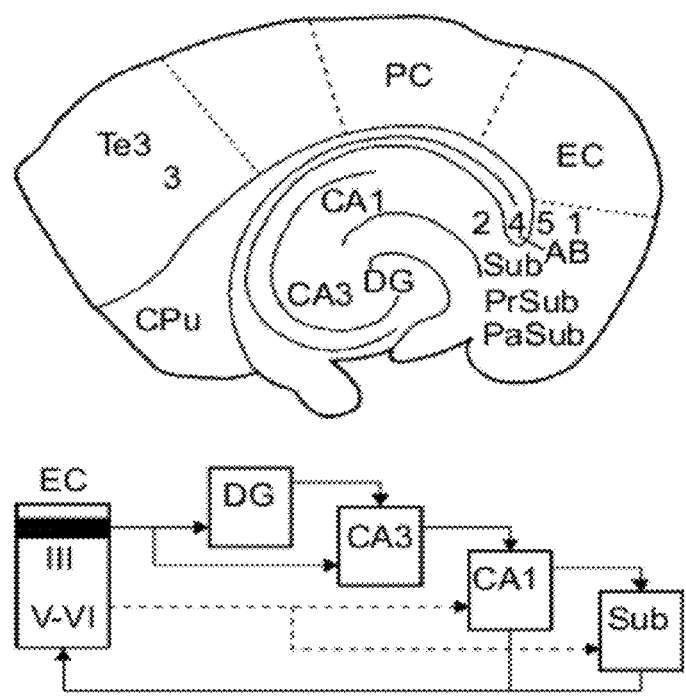

FIG. 11 is a schematic diagram illustrating the elements of the trisynaptic loop involved in generating epileptiform activity in the brain.

Figure 12:

FIG. 12 is a photograph showing a 2×8 microelectrode array for use in a rodent model of epilepsy in accordance with an embodiment of the invention, in comparison with the size of an American penny.

DETAILED DESCRIPTION OF THE INVENTION

Definitions

It is to be understood that the terminology used herein is for the purpose of describing particular embodiments and is not intended to limit the scope of the present invention, which will be limited only by the appended claims. As used herein, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs.

Epileptic Disorders

The epilepsies are a family of neurological disorders characterized by "seizures," which are transient, recurrent perturbations of normal brain function. At the physiological level, seizure activity involves the hypersynchronous activation (also known as "bursting") of a population of neurons, either in one focal area or throughout the brain, depending on the type of epilepsy. Seizures, such as epileptic seizures, are multiple stage events. The various stages include a preictal stage, an ictal stage, a postictal stage and an iterictal stage. These stages are identifiable on a traditional electroelectrogram (EEG) recording, for example as recorded from an electrode overlying an epileptogenic focus in a patient transitioning through the stages of an epileptic seizure. More particularly, the preictal stage represents the period of time preceding the onset of seizure. The ictal stage is the stage within the seizure that begins at seizure onset and lasts until the seizure ends, and the postictal stage covers the period of time immediately following the seizure. The interictal period is the period of time between seizures. The term "epileptic state," as used herein, includes the interictal, ictal, and postictal states.

Although anti-epileptic drug (AED) therapies can successfully control seizures in some forms of epilepsy, albeit often with significant side effects, many forms of the disease are refractory to current drug therapy. The two most common approaches involving electrical stimulation for controlling seizures include the vagus nerve (Cyberonics) and subdural grid stimulation (Neuropace). While each approach has been shown to produce evidence of a positive clinical outcome, neither cures epilepsy. The current clinical approach for mitigating the complexities of stimulation treatment (which include unknown neural mechanisms of stimulation, the combinatorial explosion of stimulation parameters, unknown feature vectors, and control paradigm) has been to search for 'responders' to treatment by analyzing the onset of seizure, identifying the epileptogenic zone through EEG, and iteratively adjusting the stimulation parameters until a benefit is achieved. Compared to the near immediate effects of reducing motor symptoms in deep brain stimulation (DBS) for Parkinson's disease, such a "trial and error" approach to the selection of stimulation parameters for epilepsy may not be beneficial because the effects of stimulation are difficult to interpret interictally from macroscopic electrophysiological aspects alone.

As an alternative approach, various laboratories are investigating both chronic and acute animal models of epilepsy to correlate their relevance to the human condition. One of the more common forms of epilepsy affecting human populations is mesial temporal lobe epilepsy syndrome, also known as limbic epilepsy. This condition, which is frequently unresponsive to current drug therapy, is known to originate in limbic structures of the brain such as the hippocampus and amygdala [28]. Several well-accepted animal models of this disease, characterized by spontaneous seizure activity (a clinical hallmark of epilepsy), include the chronic limbic epilepsy (CLE) model. Such models have been found useful for epilepsy research and drug discovery studies.

It is believed that as a result of this invention development of more effective therapeutic stimulation paradigms needed for treating epilepsy will be forthcoming. As further described infra, effects of microstimulation on single neurons and neural networks can be tested in animal models of epilepsy wherein the therapeutic effects can be controlled at an appropriate physiologic scale. By constraining the stimulation problem through adaptive bi-directional analysis of the stimulation response of single and multi-unit neural activity, it is possible to complement and improve upon the accuracy of current seizure stimulation methods, based on better understanding of the cellular mechanisms underlying the beneficial effects of stimulation for epilepsy. It has been recognized that abnormal single neuron bursting, measurable in microelectrode arrays, is common to both human and animal models of MTLE. The inventors have shown that these abnormal firing patterns can be tracked back to changes in single-unit activity in advance of impending seizure.

In studies described herein, the inventors have discovered that in the pre-seizure (preictal) state of epilepsy, unique predictive electrophysiological patterns can be detected using microelectrodes implanted in the brain of subjects susceptible to seizures. More particularly, electrophysiological information comprising action potentials recorded from single neurons or ensembles of neurons can be used to predict an impending seizure. Ability to detect these predictive electrical signals is an important feature of an epilepsy warning and intervention neuroprosthetic system in accordance with the invention.

Neuroprosthetic Devices

Based on these discoveries, the invention provides in one aspect a micro-control neuroprosthetic device for predicting and controlling epileptic neuronal activity. As used herein, the term "neuroprosthetic device" is meant to refer to a device used to replace or improve the function of an impaired nervous system, typically in an area of a subject's brain. A "micro-control" neuroprosthetic device is a device in which interaction with a subject's nervous system is monitored and/or controlled at the level of structures having microscopic proportions, such as individual neurons or small clusters of neurons in close proximity to one another.

Figure 1:
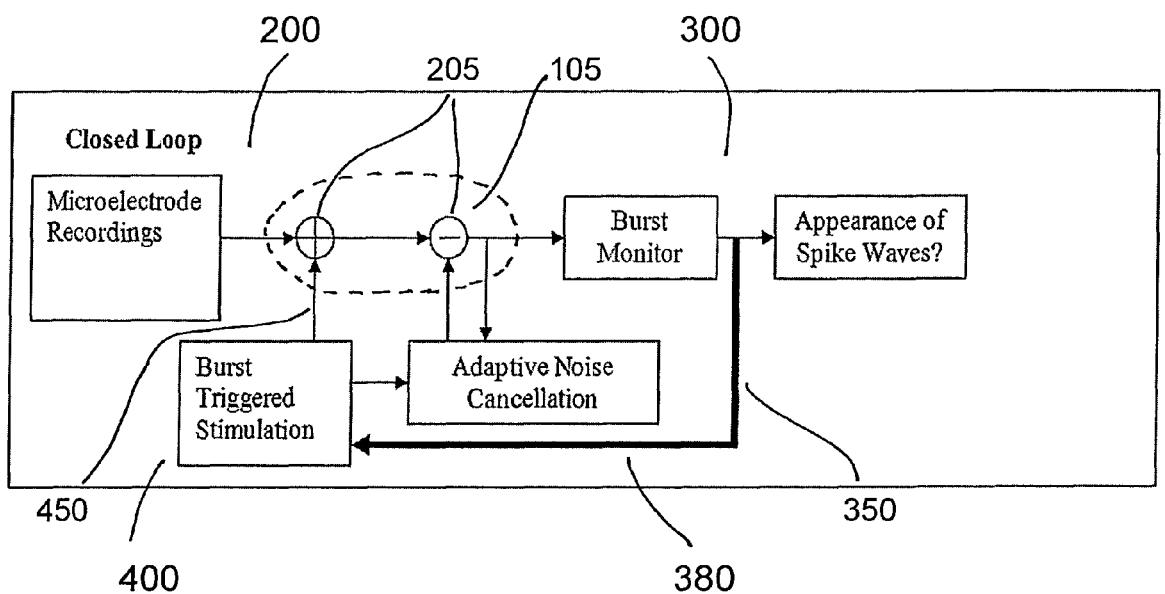
FIG. 1 is a schematic block diagram illustrating the features of a closed-loop micro-control neuroprosthetic device 100 according to an embodiment of the invention.

FIG. 1 is a schematic diagram illustrating the main components of a micro-control neuroprosthetic device 100 according to the invention. As illustrated, the device features a detection system 200 that provides a method of direct communication and interaction with single neurons or ensembles of neurons, such as those involved in an abnormal dynamical process associated with an epileptic seizure. For detection of signals, microelectrodes 205 are implanted into a neural structure 105 (typically one or more target regions suspected to be involved in epilepsy in the brain of a subject) using stereotaxic procedures well known to those of skill in the art of neurosurgery. Suitable sites for implantation of electrodes include, but are not limited to, for example, the limbic system, hippocampus, entorhinal cortex, CA1, CA2, CA3, dentate, and hippocampal commissure regions, which are known to be involved in bursting (Zugaro et al., 2005).

The electrodes of the detection system are used to record electrophysiological signals such as action potentials from single neurons or ensembles of neurons in the target region(s). A neural recording system sampling at a rate greater than about 200 Hz and up to at least 24 kHz is used to detect electrophysiological activity comprising the action potentials of single neurons and ensembles of neurons. The detection system can comprise a single electrode, but preferably includes a plurality of electrodes comprising a multi-site array. Microelectrode array technology is preferred, for example, to gain an advantage over single-site recording in spatial, temporal and spectral resolution. One preferred embodiment of a multi-electrode array contemplated for use in human subjects comprises a multi-electrode array connected to an implantable amplification and signal processing system capable of evaluating signal analysis tools, as described herein, to spatially detect bursting activity and deliver electrical stimulation therapy based on modulations in activity of single neurons or ensembles.

The analysis system 300 of the invention (also indicated as "Burst Monitor" in FIG. 1) is used to collect and analyze data obtained from the electrodes of the detection system 200. Modulations in single neuronal units and changes associated with populations of neurons are analyzed using one or more data analysis tools in the analysis system 300. These tools are based on either statistical information, data gained from models, or real-time extraction of dynamical information such as neuron firing features. The nature of the detected signals and tools used for analyzing neuronal bursting in the analysis system 300 are described in greater detail infra.

Referring again to FIG. 1, the function of the analysis system 300 is to monitor the incoming signals from the electrodes and from the collected data, in order to detect the appearance of spike waves, which signal an oncoming epileptic event. Variations in burst duration and burst frequency are monitored and either computed directly from the data, or through "feature detectors" of analysis system 300, as further described below.

In the closed-loop micro-control neuroprosthetic device 100, the analysis system 300 contains analysis algorithms that permit output signals 350 to be sent only when a neuronal or ensemble burst is detected. If this condition is met, the output signal 350 of the analysis system 300 is sent to the stimulation intervention system 400.

Closed-loop electrical stimulation afforded by the device 100 is selective, in that burst detection is computed in the analysis system 300 channel-by-channel. Accordingly, only channels with bursts will receive a stimulation pulse. The stimulus is also fed to an adaptive noise cancelling routine 380, to contend with the stimulation artifact, which can corrupt short term neural recordings [27]. Noise cancellation uses a linear filtering technique trained with the LMS algorithm to adaptively subtract out noise at known intervals.

The stimulus intervention system 400 is in communication with the electrodes 205 implanted in the neural structure 105. The intervention system 400 provides for direct micro-intervention to deliver therapy in the form of electrical stimulation to a neural cell or ensemble of neurons. Burst-triggered electrical stimulation, in the form of an intervention output signal 450 from the stimulation intervention system 400, is delivered to the target sites in the brain where the electrodes 205 are implanted, for example in limbic structures and associated neural pathways.

In some embodiments, a stimulus paradigm is used to deliver therapy directly to the recorded neural microstructure. The stimulation intervention system 400 can deliver monophasic or biphasic spike train pulses [26] directly to the neurons being monitored in the recordings. To carry out this paradigm, the implanted electrodes 205 are connected to switching headstages (recording-stimulation). A stimulus isolator delivers up to about 100 μA of current simultaneously across the electrodes (impedances up to about 1 M) with arbitrary waveforms (see Table 1, infra) of up to about 10 kHz bandwidth. Electrical stimulation frequency can either be separated into low (about 1-50 Hz) or high (about 50-200 Hz) categories.

The intensity of electrical stimulation can also be separated into low amplitude bands (for example, about 1-50 μA) and high amplitude bands (for example, about 50-100 μA). Appropriate levels of electrical stimulation have been determined in animal studies and can be adapted for use in human subjects. For example, one study of intervention has shown that low frequency stimulation consisting of 1 Hz, 50 μA for 30 s immediately before kindling in electrodes in the basolateral amygdalae of adult male rats produced positive therapeutic effects. Preemptive delivery of low frequency stimulation was shown to decrease the incidence of kindled afterdischarges [22]. In a kainic acid animal model, electrical stimulation was applied with either sinusoidal or multiphase square-waves (phasic) with varying amplitudes and periods to large regions of CA3, CA2, and CA1 pyramidal neurons. The study revealed a significant increase of activity at the positive and/or negative phase of the sinusoidal field; however, acute lesioning was observed due to extended application of DC pulses for long periods of time [23]. Two studies of stimulation frequency [24] indicate that continuous trains of rectangular constant current bipolar pulses at 100 to 800 Hz result in significantly fewer seizures than do periods of no stimulation. Additionally, stimulation frequencies of 50 Hz and lower are known not to cause any significant changes in the number of seizures [25].

Accordingly, Table 1 provides a range of discrete electrical stimulation options used by the stimulus intervention system 400 including, but not limited to, square, cine and action potential shaped waveforms suitable for micro-control of bursting activity. Additionally, the number of stimulations vs. the number of bursts is monitored in the system to avoid unstable positive feedback loops. In the event of the latter, the sensitivity of the burst monitor 300 can be either increased or decreased.

TABLE 1

Parameter Combinations for Stimulus Intervention

| Waveform Options | Frequency | Amplitudes |
|---|---|---|
| Square | 1 Hz | 1 μA |
| Sine | 50 Hz | 50 μA |
| Action Potential | 200 Hz | 100 μA |

As discussed, therapeutic local micro-stimulation is used to modulate the activity of single neurons or ensembles of neurons, thereby delaying or reducing the appearance of spike wave activity. The micro-intervention is delivered directly to target neural structures such as limbic structures and associated neural pathways in a closed-loop control system.

In some embodiments, the electrode array configured to selectively detect electrophysiological information comprising action potentials, and to output the electrical stimulation output signals is configured so as to create a plurality of channels. Providing electrical stimulation output signals includes providing electrical stimulation output signals having a desired stimulation frequency and stimulation intensity to one or more of the plurality of channels, in which in one or more channels it is determined that there is either the onset of an epileptic state, or abnormal neuronal firing.

As noted, one important advantage of the closed-loop neuroprosthetic device 100 is the capability to adjust the level or duration of electrical stimulation during stimulus delivery to the target neuronal structure, based on feedback to the analysis system 300 from the electrodes 205 implanted in the neural structure 105. Thus, following burst-triggered stimulation with release of intervention output signals 450, bursting continues to be monitored by analysis system 300. The detection of spike waves, or changes in the duration or nature of the spike waves, are used to assess the short-term efficacy of the intervention.

Figure 2:
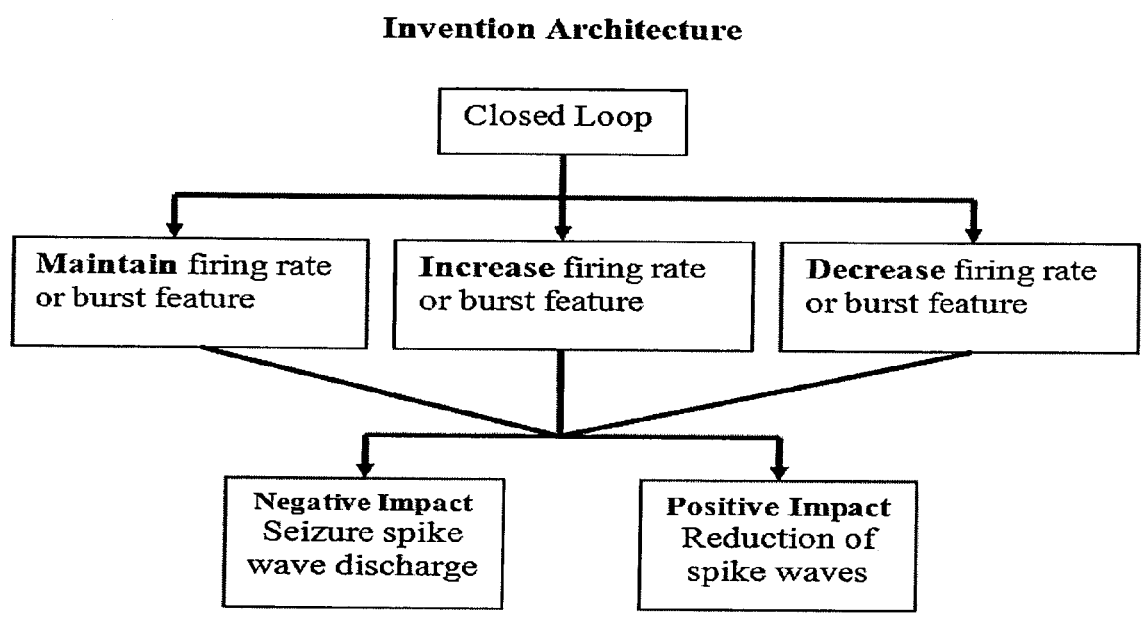
FIG. 2 is a schematic diagram illustrating control parameters monitored in a micro-control paradigm according to an embodiment of the invention.

FIG. 2 is a schematic diagram illustrating the feedback aspect of the system. As illustrated, the closed loop system can monitor significant increases, decreases, or maintenance of neuronal/ensemble activity, and modify the stimulation intervention accordingly. All three modulations in neural activity could produce a positive impact by reducing the appearance of spike waves. Accordingly, the closed-loop control advantageously permits real-time evaluation of the effects of therapeutic electrical stimulation on bursting and on the appearance of spike wave discharges, and allows for appropriate adjustment of the stimulation. Electrical stimulation of this type offers high-resolution, local specificity, and dosage delivery that can be varied rapidly, which advantages cannot be achieved by conventional drug-based therapies.

Referring again to FIG. 1, we now discuss in further detail a set of data analysis tools that are incorporated into the analysis system 300 to detect and extract bursting activity at both the neuronal and ensemble level. The analysis system 300 of the neuroprosthetic device 100 incorporates computationally efficient analysis tools, i.e., those that can respond with short time constants (about 100 ms or less). The below-described methods of the invention used to analyze neuronal bursting activity are well suited for the purpose, based on their low computational complexity or capability to efficiently extract firing features of single neurons and ensembles of neurons.

In general, the analytical methods comprise different and complementary classes of approaches: statistical, linear, and non-linear (dynamical or feedforward). Of these classes, statistical approaches provide the fundamental quantification of bursting in terms of spiking and frequency content. The linear approach utilizes well-established system identification techniques for time series segmentation. The non-linear dynamical approach addresses problems associated with non-linear time varying systems.

Figure 3A:
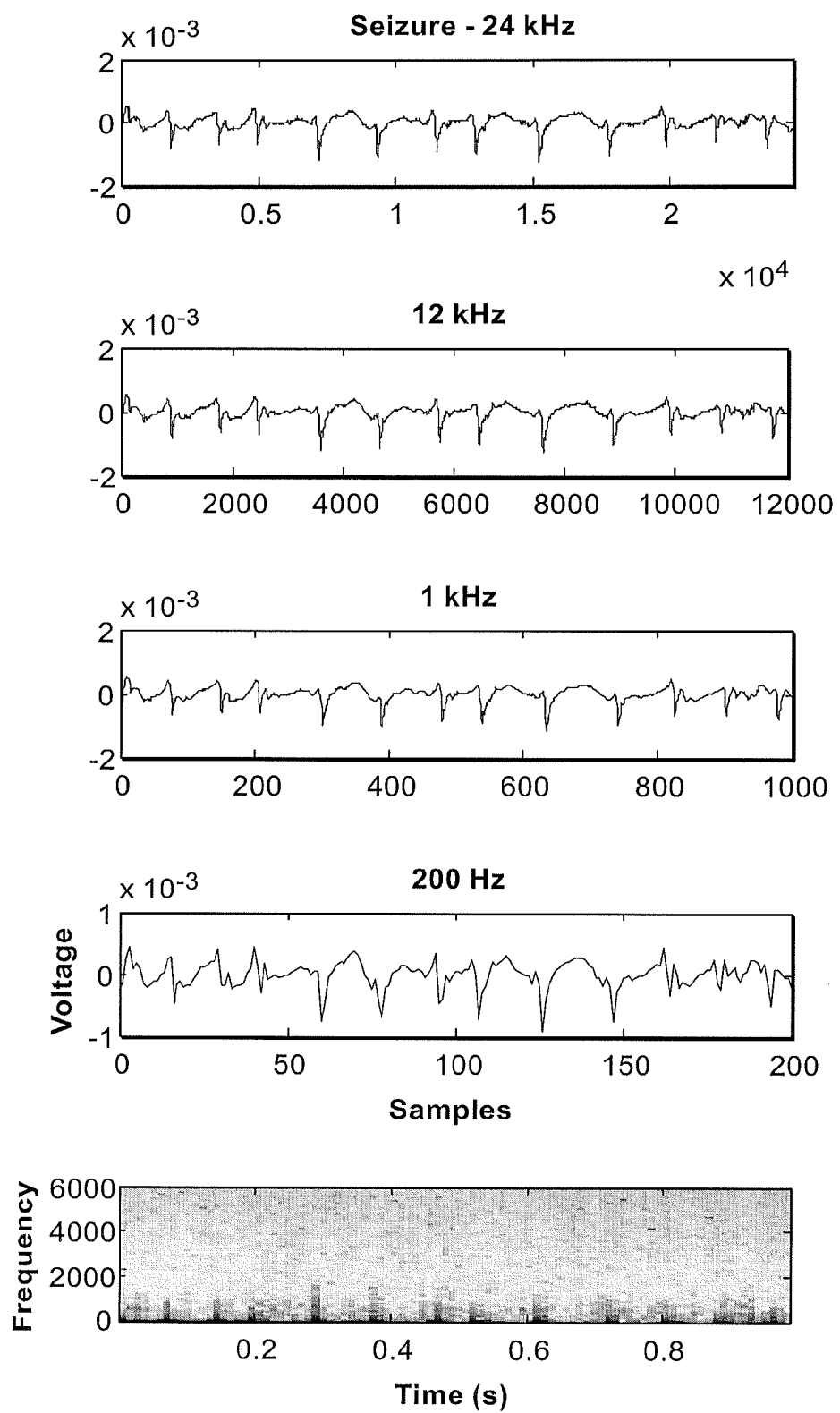
FIGS. 3A and 3B are a series of plots showing neural recordings at four frequencies recorded from microelectrodes implanted in the brain of a subject during an epileptic seizure (3A) and during the interictal stage between seizures (3B).
Figure 3B:
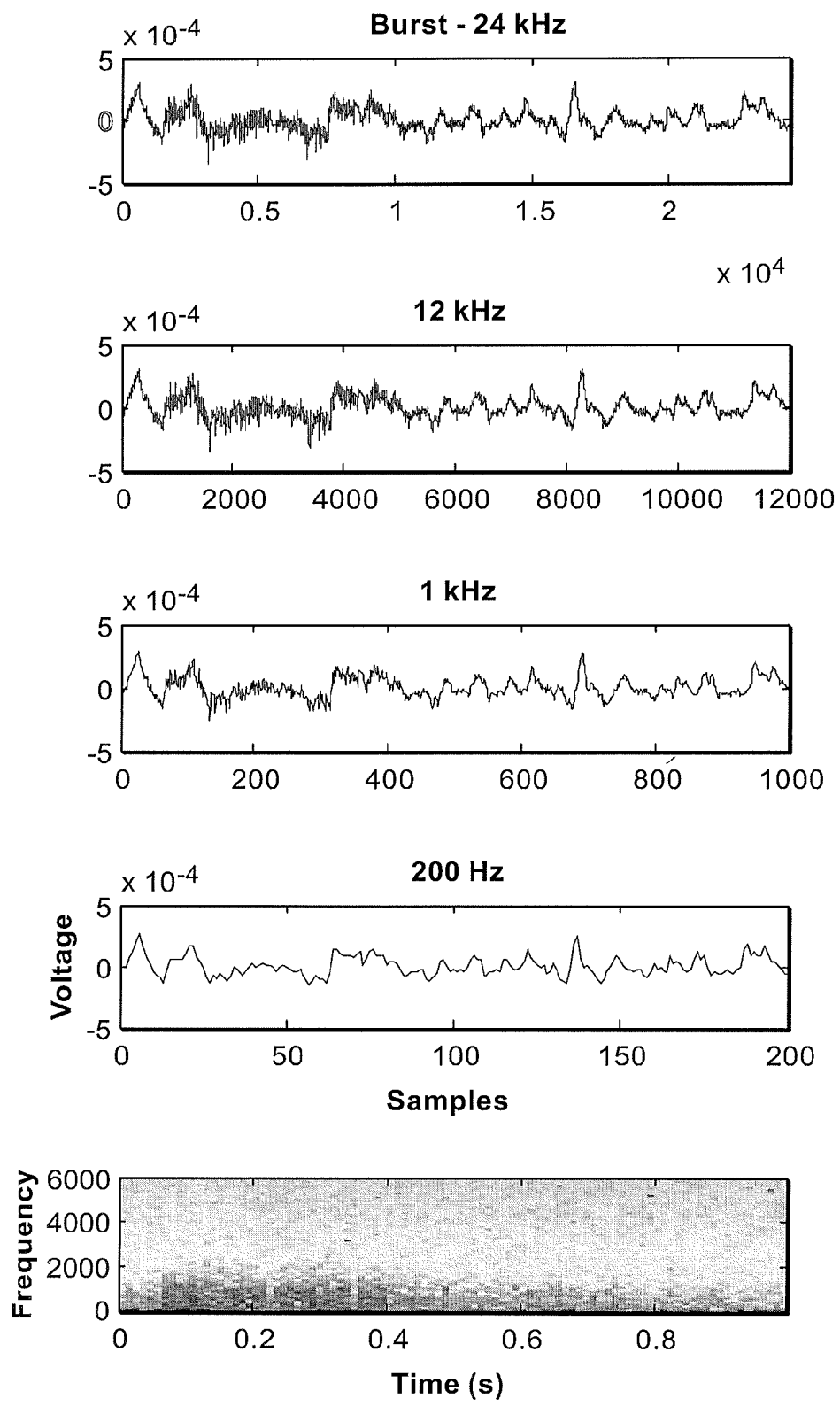

As discussed, the invention features the detection of high-frequency bursts (above 200 Hz) combined with microelectrode array technology to gain an advantage in spatial, temporal, and spectral resolution. FIGS. 3A and 3B present a series of graphs showing neural recordings taken at several frequencies (200 Hz, and 1, 12 and 24 kHz) from a microelectrode array implanted in the brain of an animal subject undergoing a grade 5 spontaneous limbic epileptic seizure, as further described in an Example, infra. FIG. 3A shows spike-wave discharges recorded during the seizure. FIG. 3B illustrates a second bursting characteristic observable in the raw recordings during the interictal state. More particularly, FIG. 3B shows high frequency interictal bursting activity seen during the initial segment for high sampled records.

Referring to FIG. 3B, the high frequency bursting characteristics are shown in raw recordings used in the closed loop system. During time segment 0.1-1.1 seconds of the 24 kHz trace, (FIG. 3B, upper plot), a pronounced increase in high frequency oscillation appears to be riding on the low frequency waveform. As can be seen by comparing the 200 Hz plot with the 1 kHz plot in FIG. 3B, the high frequency bursts only appear at sample rates above 200 Hz. This feature is in contrast with the appearance of spike-wave activity, which is similar at all frequencies tested (FIG. 3A). Importantly, the inventors have discovered that the high frequency bursts occur spontaneously throughout the latent period of epileptogenesis, and during the period of the initial spontaneous seizures. Moreover, the frequency of the bursts tends to modulate over time. Detection of these high frequency bursts is a fundamental aspect of the inventive methods embodied in the neuroprosthetic device 100.

Figure 4A:
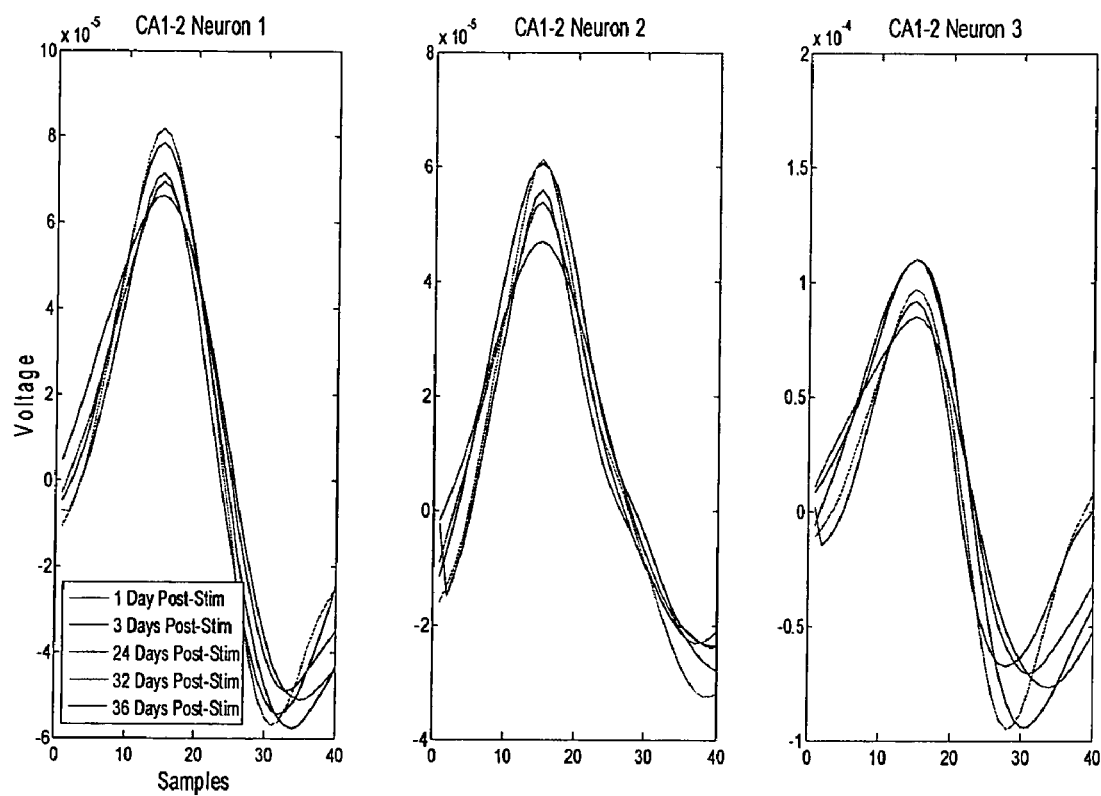
FIGS. 4A and 4B are graphs showing wave shape of action potentials of single neurons (neurons 1-3) recorded at several successive time points over one month of recording in epileptic subjects using electrodes implanted in the CA1-2 (4A) and dentate (4B) regions of the brain.
Figure 4B:
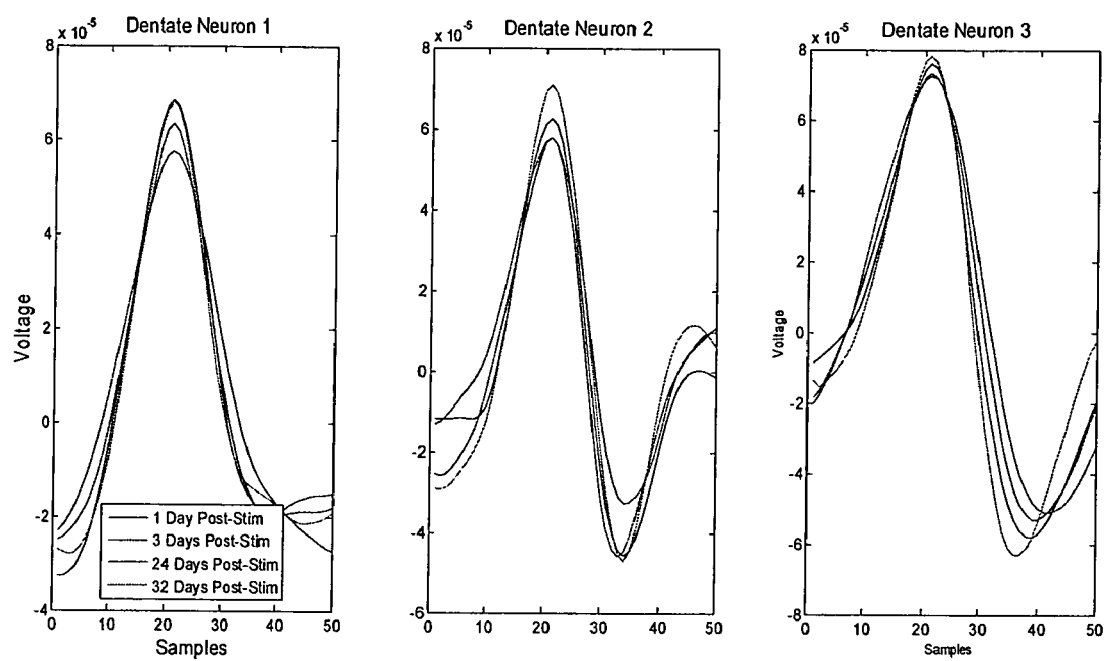

More particularly, within the burst, there are additional control features that are utilized in the invention. Some features result from the action potentials of single neurons surrounding the electrode tip. Representative traces of these action potentials taken over one month of recording are presented in FIG. 4A and FIG. 4B. More specifically, FIGS. 4A and 4B show single action potential wave shapes from repeat recordings of three neurons in the CA1-2, and dentate regions of the brain, respectively. Areas of the brain from which the recordings are taken are shown in FIG. 9. Referring again to FIGS. 4A and 4B, the analysis techniques disclosed herein allow for tracking of action potentials over long periods of time, making it possible to either mark the time of their occurrence, or the frequency of their occurrence. Raw waveforms collected at high sample rates (about 2 kHz and above)

are bandpass filtered between about 300 Hz and 6 kHz, and spike sorting methods, including template matching, principle component analysis, thresholding, feature detection, and wavelet methods, are used to detect and assign the waveforms to single neurons.

Methods for Controlling Epileptic Neuronal Activity

In one aspect, the invention provides Methods of controlling epileptic neuronal activity. A method of the invention includes at least one, and preferably all of the following steps:

(a) monitoring a neural structure and detecting and collecting electrophysiological information comprising action potentials of single or ensembles of neurons in the neural structure being monitored;

(b) analyzing the detected and collected electrophysiological information;

(c) performing a real-time extraction of neuron firing features;

(d) determining from the real-time extraction of neuron firing features the onset of an epileptic state and of abnormal neural firing; and (e) providing electrical stimulation output signals having a desired stimulation frequency and stimulation intensity to at least a portion of a neural structure being monitored responsive to said determining, to control the epileptic neuronal activity.

As discussed, the inventive step of collecting electrophysiological information includes analyzing action potentials both from single neurons and ensembles of neurons and performing real-time extraction of neuron firing features. Several methods of the invention for performing various analyses of electrophysiological information are now discussed.

Coefficient of Variation (Neuron Level—Low Complexity).

Modulations in single neuron firing are evaluated with the coefficient of variation (CV), which is the ratio of interspike interval (ISI) standard deviation to mean value. In the analysis system 300, threshold and template-based spike detection is implemented to determine the firings of single neurons. Upon computing the interspike interval mean and standard deviation, the CV is computed in real-time using window-based statistics. The CV has been used as an alternative measure to assess the amount of irregularity in neuronal firing [10]. Lower values of the CV indicate periodicity in firing and higher values tend toward bursting activity [11, 12]. Accordingly, detection of CV values about 2 standard deviations above the mean is used to determine bursting.

An overall decrease in the mean value indicates that the neurons are firing more often, but this decrease is additionally coupled with a modulation in the standard deviation, which can be used as an indicator of neuronal bursting. High standard deviations are indicative of increases in bursting; however since the number of spikes is increasing in each recording session, assessing the firing irregularity from the mean and standard deviation alone can be misleading when comparing the neuronal activity across sessions. Normal neurons have been reported to have CV values between about 0 and 1 [11, 12]. From previous studies of epileptic neurons, the CV values obtained were much greater than 1, and tended to increase over recording sessions, indicating up-regulation in the amount of irregular firing.

FIG. 5A illustrates temporal modulation of the CV as a measurement of firing irregularity of the six neurons presented in FIGS. 4A and 4B. The data show increasing slopes in the linearly fitted CV curves for four of the six neurons (FIG. 5A). Raster plots from individual epileptogenic neurons are used in conjunction with CV to assess increases in the frequency and duration of the bursting as time progresses. For example, FIG. 5B shows representative raster plots from neuron 1 in CA1-2, described above.

The CV and raster plots are used in conjunction with ISI histograms to provide a measure of firing irregularity and neuronal bursting. To provide a more complete picture of the statistics of the bursts, ISI histograms (5 ms bins) are computed for the epileptogenic neurons. FIG. 6 is a series of ISI histograms demonstrating patterns observed at various intervals (1, 3, 24, 32, and 36 days) following stimulation. The histograms are characterized by an exponentially decreasing distribution with a bump in activity at ISI interval 0.1 seconds. Spikes in the distribution are indicative of bursting activity at a rate of ten spikes per second. Compared to the first day post-stimulation, the 10 Hz bursting activity is increasing as time progresses, and can be used a control feature in the closed-loop system.

Signal Integration (Neuron or Ensemble Level—Low Complexity)

Individual neuronal activity is monitored at each electrode in real time to provide single and multiunit spike information. Due to the complex nature of spiking bursts, either bin rates of single unit activity or signal integration of the raw potentials are used for feature extraction. The integration constant is set between about 25 and 500 ms, and two thresholds are used to define the integrated burst profiles. The low threshold is used to eliminate small groups of bursting, whereas the second threshold is used to determine acceptance of a burst. In both cases, binning and population integration, a running total of burst duration and frequency is tallied.

Spectral Analysis in 300-6 kHz Band (Ensemble Level—Low Complexity)

Detection of population bursts in the raw recording is achieved with spectral analysis. Envelopes of activity containing single and multiunit action potentials such as shown in FIG. 3B present increased energy in the 300-6 kHz band (the fundamental frequencies of action potentials). Computation of the Short Time Fourier Transform (STFT) is used to provide a joint time-frequency analysis of the burst. Sliding overlapping and non-overlapping windows ranging in size between about 5 seconds and 30 seconds are used to compute the STFT of each channel. Threshold detection of the peaks in the band are used as indicators of bursting. Statistical comparisons of the frequency representations that occur during a study of long-term variation in neuronal firing rate and bursting are computed.

Signal Energy (Ensemble Level—Low Complexity)

One aspect of the analysis system 300 of the neuroprosthetic device 100 is analysis of signal energy. The studies of high frequency oscillations described herein demonstrate that signal energy increases during bursts. Signal power (signal energy) has also been used to predict seizures and to detect physiological sleep states in patients with temporal lobe epilepsy [5]. In the analysis system 300 of the invention, average signal energy is calculated with both the conventional measure of energy and the Teager algorithm. The conventional measure of signal energy considers contributions from all frequencies of a signal in equal fashion. Teager energy, by contrast, weighs contributions of differential frequencies in a non-uniform fashion, emphasizing higher frequencies by square law weighing [13]. Teager energy has been found to be useful to detect seizures in patients with temporal lobe energy [14]. This method is suitably adaptable to time-varying signals, is relatively simple to execute, is physically discerning, and is useful for defining states.

Match Filter (Ensemble Level—Low Complexity)

In some embodiments, the analysis system 300 of the invention is further adapted to perform match filtering, an approach used in detection theory. In the implementation of the method, representative bursts in the recordings are used as templates to detect additional bursts. The method prescribes convolving the impulse response of the signal to be detected with the time series of interest. For example, the signal to be detected is a bursting envelope (as shown in FIG. 8B). By taking the point-by-point multiplication and integration of the burst snippet with the neural recording at every time point, a sliding correlator is created wherein a peak in correlation indicates the location of a burst. Even in the presence of noise, the match filter has been shown to be robust in signal detection.

Linear Predictive Models (Neural or Ensemble Level—Moderate Complexity)

Some embodiments the analysis system 300 of the invention are adapted to perform linear predictive modeling. It is generally accepted that a degree of redundancy exists among the populations of neurons (ensembles) and that interpretations based on single unit analyses can be extended to the ensemble [31]. To assess the ensemble's contribution to the epilepsy process, the invention includes a complementary approach for extracting features from neuronal activity from the mesoscipic local field potential level using the same microelectrodes used for the single unit analysis. This analysis emphasizes features of the action potential in the raw recordings, but does not extract the precise firing of each neuron. Accordingly, analysis is presented on potentials that are only bandpass filtered between 300 Hz and 6 kHz (no spikes are detected or sorted). The field potentials generated in this way contain a much larger diversity of neuronal activity both from neurons close to and distant from the electrode tip.

The methods utilized in the analysis system 300 include the signal processing methodology of linear autoregressive (AR) modeling to quantify the local time structure of the recorded time series. The purpose of fitting AR models to the field potentials is to capture within them the spike bursting rhythmicity throughout the temporal evolution of a recording session and between sessions. In many ways, local bursts in neuronal activity are analogous to single words in speech. Therefore, a speech analysis method called linear predictive coding (LPC) which has been a predominant method for estimating basic speech parameters and for representing speech [18] is used in the system 300 to analyze neuronal activity. In this approach, a functional set of models is constructed, each accurately capturing short segments of the field potential activity.

FIG. 7 is a schematic diagram of the analysis paradigm based on linear AR modeling. The system that is generating the waveforms s(t) of the two contiguous segments $t_0$-$t_1$ and $t_1$-$t_2$ in the time-series is identified. Using the method of LPC coding, a model is constructed that can predict future samples of the time series from the statistics of past neuronal potential values. Segmenting and modeling in this way generates a series of models that evolve over time as the statistics of the original signal change. The model parameters (coefficients) are used to assess how the representation of the signal is changing in time.

The method prescribes windowing the signal of interest and approximating future samples as a linear combination of previous samples using the equation:

$$\tilde{s} = \sum_{k=1}^{p} \alpha_k s(t_N - t_{N-k})$$

where $s(t_N)$ is the original signal at sample N; $\tilde{s}(t)$ is the predicted signal; $\alpha_k$ are the predictor coefficients; and p is the prediction order (the number of previous samples used to compute the current prediction). A unique set of predictor coefficients for any given signal is determined by minimizing the sum of the squared differences between the actual samples and the linearly predicted ones. These predictor coefficients serve as dependent variables. The autocorrelation method for LPC is used to calculate the predictor coefficients and the Levinson-Durbin recursion is used to solve this system of equations for $\alpha$.

FIGS. 8A and 8B present results of linear predictive modeling shown at various times before and after stimulation, assessed in four quadrants (Quadrants 1-4). FIG. 8A shows parameter clustering over time. FIG. 8B shows representative waveforms from models shown in Quadrants 2-4 of FIG. 8A. Referring to FIG. 8A, examples are shown of the clusters of the first and second coefficients of all the AR models for ensembles of neurons. Each session's cluster comprises 200 AR models, which represent the system identification of about 3000 seconds of data, which is also inclusive of the segments used in the analysis. As with any AR modeling application, the appropriate choice of window size and prediction order is evaluated.

In the system illustrated in FIG. 8A, 15-second non-overlapping windows and a prediction order of 2 are selected. The interpretation of the results presented herein is consistent with other choices of window size (5 or 30 seconds) and larger prediction orders of 3. As can be seen, the distribution of model coefficients is quite distinct for each recording day. For normal neuronal activity (for example, as shown at 43 days pre-stimulation), neuronal activity is very consistent, as indicated by the tight cluster of model coefficients with small variance, located in Quadrant 4 of the plot (FIG. 8A, upper left plot). However, one day post-stimulation several of the LPC models are significantly different than the baseline, indicating that the firing activity for those particular model segments is statistically different than baseline (FIG. 8A, upper right plot). As time progresses (e.g., at 3, 24, 32, and 36 days post-stimulation), an increasing density of models falls within Quadrants 2 and 3, as shown in FIG. 8A.

To assess the differences in time-series segments represented by the models, we plot the filtered waveforms from Quadrant 2 (model: −1.83, 0.90), Quadrant 3 (model: −1.74, 0.83), and Quadrant 4 (model: −1.67, 0.80). FIG. 8B illustrates representative waveforms from models in each of Quadrants 2-4 shown in FIG. 8A. Referring to FIG. 8B, it is seen that the models in Quadrant 2 are represented by large amplitude bursting activity lasting between 7 and 10 seconds. In contrast, the activity in Quadrant 4 contains all low amplitude activity with a few single unit spikes. Intermediate to the activity in Quadrants 2 and 4, Quadrant 3 contains a mixture of 15-second duration of bursting, but at lower amplitude.

The spread of the LPC model clusters indicates that there is a continuous spectrum of activity that spans the three extremes presented in FIG. 8B. A method to quantify the temporal evolution of the modeling computes the percentage of models in each of the aforementioned quadrants over time (Table 2). Referring to Table 2, it is seen that the overall trend in the modeling indicates that the ensemble neuronal activity is increasing its bursting frequency and duration. In the time domain, the AR modeling is reporting more models corresponding to the spindle wave shapes shown in the left subplot of FIG. 8B. This interpretation of bursting frequency is supported by a decrease in the percentage of models in Quadrant 4 (baseline), with an increase in the percentage of models in Quadrant 2 (bursting). With respect to bursting duration, the increase in the Quadrant 3 models over time indicates longer timespans.

TABLE 2

Distribution of Model Parameters Over Time.

Percentages of Models in each Quadrant

| | 43 days pre-stim. | 1 day post-stim. | 3 days post-stim. | 24 days post-stim. | 32 days post-stim. | 36 days post-stim. |
|---|---|---|---|---|---|---|
| Quadrant 1 | 0 | 0 | 0 | 0 | 0 | 0 |
| Quadrant 2 | 0 | 6.5 | 8.5 | 7.0 | 29.1 | 21.1 |
| Quadrant 3 | 0 | 11.3 | 23.2 | 19.0 | 30.1 | 29.5 |
| Quadrant 4 | 100 | 82.3 | 68.3 | 73.9 | 40.8 | 49.4 |

Non-Linear Predictive Models (Neural or Ensemble Level—High Complexity)

Some embodiments of the analysis system 300 of the neuroprosthetic device 100 of the invention are adapted to perform non-linear predictive modeling. As discussed above, the invention includes an extension of windowed linear modeling for burst detection using clusters of model coefficients and changes in model state. However, some alternate embodiments of the invention employ more complex non-linear functional forms to predict the time series, in order to utilize fewer models, or models with state transitions capable of representing the structure of spike trains or fields produced during bursting time periods in the model parameters.

Non-linear models, such as the feedforward Time-Delay Neural Network, or the non-linear feedback (dynamical) Recurrent Multilayer Perceptron (RMLP) models [19, 20] have the capability of representing with reduced error the non-linear manifold that contains recordings from the hippocampal input. Using non-linear, time series modeling of spike train data in the context of Brain Machine Interfaces, we have previously reported that the recurrent neural network (RMLP) [21] is one of the most parsimonious models (i.e., requires fewer parameters) to capture dynamically time structure at different time scales in time series. The state feedback of recurrent systems allows for continuous representations on multiple timescales. Here, the determination of bursting can either be quantified in the parameter space of the non-linear model by computing multidimensional Euclidian distance measures, or by detecting state transitions of the hidden layers of the network.

A second non-linear model incorporated in some alternate embodiments of the invention is the Time-Delay Neural Network (TDNN) model. Although its memory structure is not as sophisticated as that of the RMLP, windowed time-series prediction training is less complex but still capable of preserving model parameters or state transition bursts.

EXAMPLES

The invention is further illustrated by reference to the following non-limiting Examples.

Example 1

Materials and Methods

The following methods are useful in testing and practicing various aspects of invention.

1.1 Electrode Implantation in Animal Model of Spontaneous Seizures. Adult male Sprague-Dawley rats are premedicated with xylazine and anesthetized with isoflurane in oxygen and placed in a Kopf stereotactic frame. A midline incision is made in the scalp and all soft tissue is loosened from the dorsum of the skull. A craniotomy is drilled for electrode placement such that the long axis extends from about 1.7 mm lateral to 3.5 mm lateral from the bregma, and the dura is removed. Up to about 16 microwire recording electrodes (50 μm polyimide insulated tungsten microwires) are chronically implanted into CA1-2 (about −3.8 mm posterior, 1.7 mm lateral (left) of bregma) and dentate of the hippocampus. The recording sites are involved in the generation of epileptic discharges [30].

The electrodes are lowered (measuring from the surface of the cortex) at a rate of about 1 mm/20 minutes, to minimize tissue damage. Electrodes are configured, for example, in four bundles (two electrodes per bundle) arranged in a rectangular pattern to conform to the morphology of the hippocampus. On the long axis of the rectangle, each electrode in the bundle is separated by about 200 μm, whereas on the short axis each electrode is separated by about 400 μm. The electrode bundles are custom fabricated using a single Omnetics (Minneapolis, Minn.) low profile connector.

A second electrode, bipolar twisted Teflon-sheathed stainless steel, about 330 μm diameter, is implanted in the contralateral posterior ventral hippocampus (about −5.3 mm posterior, 4.9 mm lateral (right) of bregma, 5 mm ventral) for stimulation into status epilepticus (Lothman, Bertram et al. 1990). All electrodes are chronically secured with dental cement and anchored to about four micro screws driven into the bone of the skull.

1.2 Induction of Status Epilepticus (Hippocampal Stimulation). Approximately one week following surgery to implant electrodes, the bipolar twist electrodes are used to induce self-sustained limbic status epilepticus. A suprathreshold stimulus of about 240 μA is delivered for about 60 minutes using 10 sec trains of about 50 Hz 1 ms (duty cycle) bipolar square waves every 12 seconds. Typically, immediately following the onset of stimulation, the animal demonstrates "wet dog shakes" and seizes several times during the procedure. After stimulation, the animal seizes periodically for 1 hour, and slow wave potentials are observed in the EEG for 12 hours thereafter. Once spontaneous seizures develop, the severity of seizures is graded. Seizure detection is performed visually using both behavioral (video) and electrographic monitoring, for example by three expert evaluators, e.g., a pediatric epilepsy neurologist, a behavioral neuroscientist, and a biomedical engineer. To determine a seizure grade, the three independent evaluators corroborate their determination of the electrographic and behavioral recordings. A behavioral seizure score (BSS) is determined using the standard Racine scale (0, no change; 1, wet dog shakes; 2, head bobbing; 3, forelimb clonus; 4, forelimb clonus and animal rearing; 5, rearing and falling). The EEG seizure duration for this animal model lasts between about 10 and 60 seconds. Most seizures are characterized by a low amplitude hypersynchronous fast beta activity that evolves to higher amplitude polyspike alpha waves, followed by spike and wave theta activity and a postictal spike wave low amplitude delta. Behaviorally, the animal is rearing and falling on its back. Historically, we have observed 80 percent of our animals to spontaneously seize. Other laboratories have also reported between 75 and 100 percent of the animals to seize (Lothman and Bertram 1993; Bertram 1997).

1.3 High Resolution MR Imaging for Electrode Target Verification and Pathology Location. Following participation in an epilepsy study as described herein, the electrodes are removed, and the animals are perfused with 10% formalin, and the intact fixed brain is then extracted. Prior to MR imaging, the brain is soaked in phosphate buffered solution (e.g., PBS) for about 24 hours to wash out residual fixative.

For MR imaging, the brain is placed in a 20 mm tube containing a fluorinated oil (Fluorinert; 3M Corp.) and imaged, for example in a 17.6 tesla, 89 mm bore Bruker Avance MR instrument (Rheinstetten, Germany). In a typical experiment, images are acquired with a 3D gradient echo pulse sequence with a repetition time of about 150 msecs, gradient echo time of 15 msecs with one (control animal), two (test animal #2) or six (test animal #1) signal averages. The image field-of-view is about 30 mm×15 mm×15 mm, in a matrix of about 400×200×200.

The data is acquired in a total data acquisition time from about 1 hr 40 min, 3 hrs 20 min, or 10 hrs, depending on the number of signal averages. We find that two averages (3 hrs 20 min) provide the optimum compromise between signal-to-noise ratio and measurement time. MR images are acquired with a resolution of about 75×75×75 $\mu m^3$. A 3D Fourier transformation is applied to the acquired data matrix, to produce a 3D image, which is then interpolated by a factor of two in each dimension to produce an image with a display "resolution" of 37.5 mms.

The above method using high-field, high-resolution MR imaging is effective for visualizing the location of pathology and the track of the stimulating and recording electrodes in rat brains following excision and fixation. With the high signal-to-noise ratio available with a high magnet field (for example, 17.6 telsa), three-dimensional MRI setup, images are acquired with excellent resolution, allowing for clear visualization of brain structures, hippocampal pathology, and tracks of the electrodes within the brain.

1.4 Electrophysiological Data Collection. Multichannel neuronal potentials are collected synchronously, for example, over about 75 days while the animals are engaged in sleep or in quiet exploration in a one foot diameter cylindrical acrylic cage. Several time points are selected for recording sessions in the course of the study. For example, baseline recordings are made between about 10 and 28 days post-surgery, and at several time points, for example, at 1, 2, 20, 28, and 32 days following stimulation. Neuronal activity is recorded over the timeline using a Tucker-Davis (Alachua, Fla.) Pentusa™ neural recording system sampling at 24,414.1 Hz.

The potentials are digitized with 16 bits of resolution and bandpass filtered from about 0.5 to about 12 kHz. Recordings are stored in their most raw form (only wide-band filtering is applied), providing for the greatest variety of post-processing. High sampling rates are needed to accurately represent action potentials from single neurons for later spike sorting. Depending on the type of analysis to be done, only the occurrences of the action potential times can be saved, to reduce data storage. For data modeling of both single neuron and ensemble activity, both spike times and raw data are saved. Demanding sampling rates and simultaneous multi-electrode recording over months under this protocol can generate over a terabyte of data for each animal. Accordingly, data handling, post-processing, and analysis require the best currently available computer hardware consisting of dual processor servers with two gigabytes of RAM. With such systems it is possible to continuously monitor spontaneous seizures from behaving animals with resolution from the ensemble field potential level to the single neuron level.

Example 2

Microstimulation and Neuromodulation Studies in Animal Models of Epilepsy 2.1 Experimental Animals and Procedures. Preclinical investigations and data collection techniques used to evaluate the effects of stimulation as described herein require identification of an appropriate animal model. One such model is a chronic limbic epilepsy model. The rat chronic limbic epilepsy (CLE) model is a spontaneous seizure model that is created by inducing prolonged seizures (status epilepticus) through direct electrical stimulation of the hippocampus. After a period of several weeks to a month of recovery, the animals begin to have spontaneous seizures that last for the rest of their lives [B2-B4]. Rat CLE is considered a good model of temporal lobe epilepsy since it is characterized by spontaneous limbic seizure activity, which is the clinical hallmark of MTLE. Furthermore, in rat CLE both the seizure locus and the pathological changes in the limbic system of the animals reflect what is found in the human pharmacoresistant MTLE [B4-B6]. The mechanisms by means of which spontaneous seizures occur in the CLE model and the extent to which microstimulation can influence them are not yet clear and is a point of investigation in this proposal. On the basis of a series of experiments using different agonists and antagonists of both GABA-A and B receptors, Lothman [B7] suggested that GABAergic mechanisms can influence seizure initiation and are critical in the termination of seizures. Recently, in a series of experiments aimed at clarifying the pathophysiology of this chronic model of temporal lobe epilepsy, a number of relevant changes observed at least 1 month after the status epilepticus were described: monosynaptic excitatory postsynaptic potentials (EPSPs) evoked in CA1 pyramidal cells, but not in the granule cell of the dentate gyrus in post-CHS tissue were always longer than those in control tissue [B8].

2.2 Selection of the State Variables. We utilize technology for reliable recording of the spike trains of single neurons with arrays of multiple microelectrodes inserted directly into the limbic system of an experimental animal [B9]. For this purpose, bundles of very fine wires (e.g., about 50 μm diameter) are inserted into the entorhinal cortex, dentate gyrus, and the pyramidal cell layer (CA1-3) of the rat. The locations of the tips of the wires are adjusted to isolate the spike trains of multiple neurons from each tip (usually within 200 μm of the cell body). The spikes from single neurons are identified by template matching algorithms [B10] of the action potential waveforms sampled at 24,414.1 Hz (spike durations are typically 1 ms), using a Tucker-Davis (Alachua, Fla.) Pentusa neural recording system. The extracellular recordings are bandpass filtered from 300 to 6 kHz and digitized as 1's for spikes in sequences of 0's for each identified neural spike train. High sampling rates are needed to accurately represent and discriminate action potentials from single neurons.

The parallel and distributed processing capabilities of the brain suggest that neural information is spread across populations of neurons [B11]. Therefore, simultaneous recordings from large numbers of neurons should extract more information compared to serial single neuron recordings. This basic hypothesis of systems neuroscience has sparked the development of a variety of invasive recording techniques and electrode arrays that are capable of recording the activity of tens to hundreds of neurons chronically for long periods of time. The functionally representative modulation of activity in neural assemblies is the signal of interest. The development of the aforementioned methods has allowed neural recordings to be analyzed at the level of neuronal populations as well as the single neuron level.

Because a large collection of neurons is recorded simultaneously, one can directly measure the modulations in activity that occurs in neuronal populations during a variety of epilepsy states [B12]. The first step in developing the functional relationships in the neuronal groups has been the identification of physiological signals that modulate and correlate with the behavioral outputs or sensory inputs of the organism. Research in other fields supports the use of multi-microelectrode techniques to interact with large groups of neurons including: modulation of photoreceptive cells for generating phosphenes in retinal implants [B13], reading pyramidal cell rate codes in motor systems [B14], stimulation of the tonotopic organization of the neurons for cochlear implants [B15, B16], and disruption of abnormal basal ganglia neuronal firing in deep brain stimulation (DBS) for Parkinson's disease [B17]. This ability to statistically account for the modulation in neuronal populations provides a more representative assessment of assembly activation than acute recordings of the same single neurons over many trials. The disclosed methods utilize such a highly resolved spatiotemporal approach for prediction an prevention of epileptic seizures by measuring complex changes in neuronal population activity recorded over many time frames, ranging from fractions of seconds to several hours or days.

Our earlier studies demonstrate our ability to stimulate single neurons within the hippocampus and to measure their response over multiple recording days. In the hippocampus, features such as spike duration, firing rate, spike waveform, and the local field relations can be used to separate pyramidal cells from interneurons [B12, B18, B19]. At the core of our recording technology is a switchable headstage that features high-voltage, low-leakage solid-state relays to allow remote switching between stimulation and recording from the same electrode.

Figure 10A:
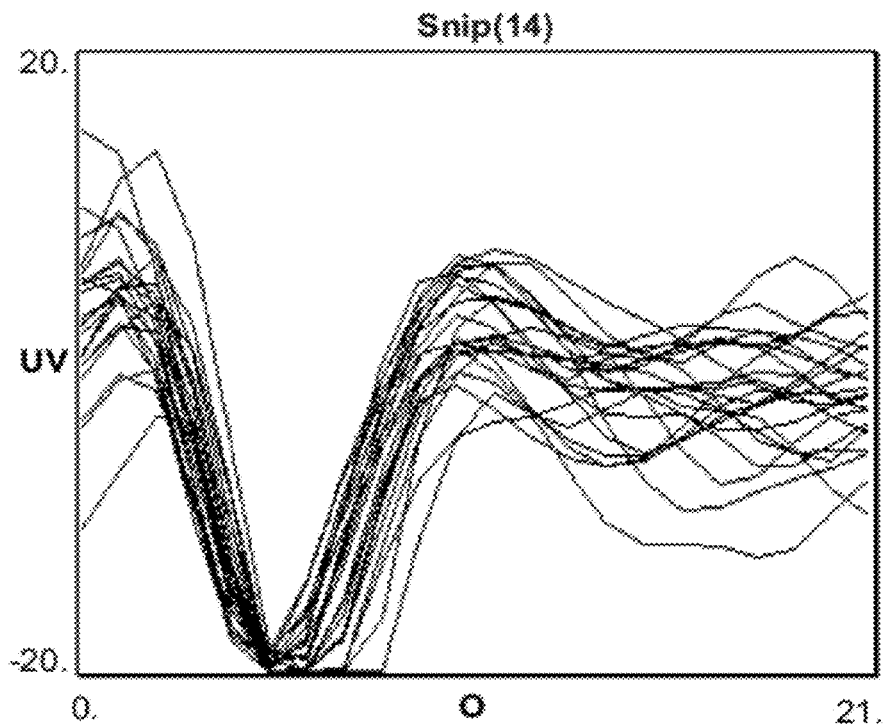

2.3 Evaluation of Microstimulation Studies. To evaluate the effects of microstimulation, we performed an intermixing study that varied the frequency and duration of the stimulus in a control animal with chronically implanted microelectrode array consisting of 16 electrodes. At the time of testing, this animal had been implanted for over ten months, and produced single unit recordings as shown in FIG. 10A. Daily neuromodulation testing sessions were conducted by randomly assigning the stimulation parameters of frequency (0.3, 3, 30, 130, 300 Hz) and duration (1, 5, 10 seconds). Each stimulation setting was repeated three times during a recording session. The simulation protocol was repeated over four consecutive days. Microstimulation pulse trains consisted of cathodic first, charge-balanced, biphasic square-wave pulses (2 ms pulse width) delivered at 100 µA. These stimulation, frequencies, duration, and intensity was chosen because of their use in DBS and VNS therapies [B20]. The duration of the biphasic pulse was chosen to match the duration of an action potential. The current spread for the intensity of stimulation used is computed to be 150 µm while the electrode array contained a spacing of 250 µm between electrodes [B21, B22]. The microstimulation stimulus intensity was confirmed using a 330Ω resistor circuit prior to testing. A cranial stainless-steel screw served as the stimulation return pathway.

For each stimulation setting, neuronal firing was recorded for 30 seconds before and 30 seconds after stimulation so that the causal differential in firing rate could be assessed. To minimize the influence of successive stimulation parameters, the tissue was allowed to rest for 30 s between stimulation. Additionally, the settings were randomized.

Figure 10B:
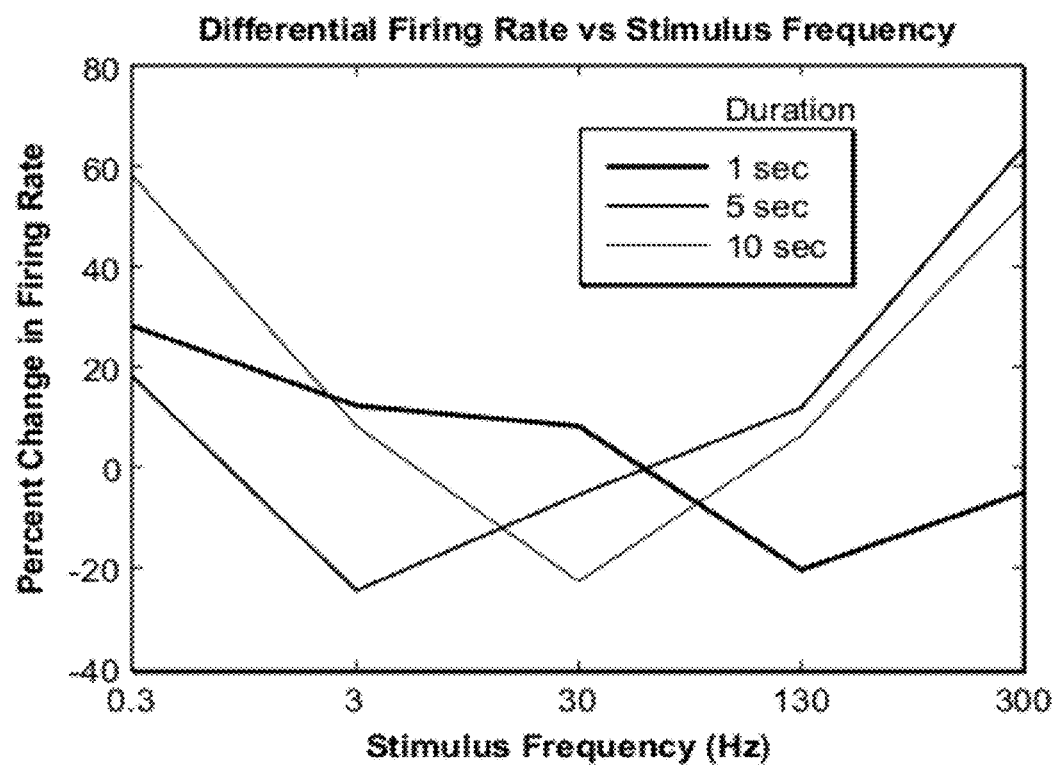

The results of the stimulation study are presented in FIG. 10B, in which is plotted the percent change in firing rate resulting from each setting of frequency and duration. Each data point compares the average percent change in firing rate for the neuron shown in FIG. 10A. All but three of the data points are above the line of zero change, indicating an overly excitatory effect of microstimulation. Each duration setting of stimulation created a parabolic shaped curve over the frequency range studied, indicating a point of maximal inhibition.

2.4. Significance. This results of this study demonstrate that the inhibitory effect of stimulation does not simply linearly increase with frequency, as has been previously reported. The study also shows the feasibility of microstimulation within the hippocampus. Importantly, the results show that the firing rate of a single neuron can be modulated chronically and that stimulation at the prescribed level does not cause cell death. This provides proof of concept that electrical microneuromodulation may provide the necessary control mechanism for treatment of epilepsy in human patients. These studies also demonstrate that microstimulation in general produces an excitatory effect; however, certain combinations of stimulation frequency and duration can produce greater than 20% decrease in firing rate.

Example 3

Studies of Epileptic Bursting in Animal Models 3.1 Bursting Neurophysiology in Connection t with Epilepsy. For nearly thirty years, epileptologists have been studying macroscopic electroencephalogram (EEG) recordings from the scalp to obtain global and local measures of scalp potentials using a variety of linear, nonlinear, and dynamical computational measures [B23-B27]. On the surface of the cortex, electrocorticographic (ECoG) electrode arrays have been used in the clinical setting to determine epileptic foci, but the analysis of the signals has been conducted at the level of the system and circuit mechanism [B28, B29]. Recently, with the advance of multi-site microelectrode technology, acute preparations of hippocampal recordings have provided data on neuronal firing related to the epileptic condition [B30]. In conjunction with in vivo recordings in both animals and humans, slice physiologists have performed elegant experiments to infer the normal and bursting responses of single units in excised tissue [B31, B32]. This study has focused on potentials in the 300 Hz to 6 kHz range that contain the action potentials of single neurons. The identification of abnormal neuronal bursting has been reported in the epilepsy literature and is a recognized feature of epileptic state [B33-B38]. Dramatic increases in firing rate have been reported in the piriform, perirhinal cortex [B39] and amygdala during the interictal period [B33]. A challenge that has remained is to determine what neural engineering principles can be used to cause disruption of the bursting to produce a therapeutic effect (reduction in seizure frequency/duration).

3.2 Longitudinal Study of Bursting in Epileptogenic Animals. To study the development of bursting in animals models of TLE, we conducted an extensive longitudinal study of single neuron and network firing during the latent period of epileptogenesis. Multi-channel neuronal potentials were collected synchronously over 73 days at the University of Florida McKnight Brain Institute while animals were engaged in either sleeping or in quiet exploration in a 1 ft. diameter cylindrical acrylic cage. We began with normal Sprague Dawley rats and induced self sustaining status epilepticus. To quantify the electrophysiologic changes that occur during the latent period of epileptogenesis, we recorded continuously (24 h/day) from microelectrode arrays placed throughout the hippocampus. After the initial insult of status epilepticus, the animal model undergoes a series of cellular and network changes that lead to spontaneous seizures that occur 6 weeks post status. Depending on the type of electrophysiological analysis being pursued, it is possible to just save the occurrences of the action potential times. For analysis of both the single neuron and ensemble activity for data modeling, both the spike times and the raw data were stored. With such demanding sampling rates and simultaneous multi-electrode recording over a period of months, the experimental protocol generated over a terabyte of data for each animal.

FIGS. 3A and 3B, described supra, illustrate representative electrographic traces collected from the animals at the native sampling rate and down-sampled after lowpass filtering in steps down to 200 Hz. More specifically, FIG. 3 shows neural recordings and spectrograms from CA1-2 (1 second), illustrating spike-wave discharges from a grade 5 spontaneous limbic seizure (FIG. 3A), and high frequency interictal bursting activity seen during the initial segment for records sampled at 1 kHz and above (FIG. 3B). In FIG. 3A, spike-wave activity is shown from a grade five seizure recorded during the last monitoring session. The electrographic seizures were characterized by the onset of paroxysmal, increased amplitude spike-wave discharges that showed an evolutionary pattern of a gradual slowing of the discharge frequency and subsequent post-ictal suppression. The bottom plots in FIGS. 3A and 3B contain the spectrograms of the raw neural recordings. Peaks in the energy are seen at the higher frequencies when the potentials form a spike-wave discharge.

The waveforms presented in FIG. 3 resemble classic epileptic activity observed by "slice physiologists" using microarray technology [B30, B40]. It is interesting to note that despite the sampling rate the spike-wave discharge frequency remains distinct; therefore, for identifying spike-wave seizure activity it may be concluded that 200 Hz is more than sufficient. As the sampling rate is increased, additional details can be observed riding upon the large amplitudes in the discharges.

In FIG. 3B we present a second bursting characteristic of the raw recordings that was observed during the animal's interictal state. In this example during time segment 0.1-1.1 seconds of the 24 kHz trace, a more pronounced increase in high-frequency oscillation (a burst) appears to be riding upon the low frequency waveform. High frequency bursts only appear at sample rates above 200 Hz (compare 200 Hz plot and 1 kHz plot of FIG. 3B), which contrasts with the observations of the spike-wave activity in FIG. 3A. A spectrogram at the bottom of FIG. 3B demonstrates a large increase in energy up to 2 kHz. The bursts were observed to spontaneously occur throughout the latent period of epileptogenesis and during the period of the initial spontaneous seizures. Moreover, the frequency of the bursts tended to modulate over time.

The nature and fundamental properties of these bursts and their association with the hippocampal neural network activity related to evolution of seizures in the animal model is further described below.

The presence of high-frequency bursts (above 200 Hz) and the use of microelectrode array technology naturally lead to the analysis of neuronal activity on the single neuron level. Investigation of the bursts in the raw recordings sampled at 24 kHz revealed the presence of single unit neuronal activity in both the CA1-2 and dentate neurons. To emphasize the frequencies contained in action potentials, the raw waveforms were bandpass filtered between 300 Hz and 6 kHz. Features such as spike duration, firing rate and spike waveform were used to separate pyramidal cells from interneurons. To extract single neuron activity, the first step of the analysis involved the setting of a voltage threshold for each of the microelectrodes. This threshold was set by the experimenter using Spike 2 (CED, UK) through visual inspection of the digitized time series. A set of unique templates was constructed from the threshold waveforms based upon the width and a minimum and maximum amplitude associated with it. If more than 80 percent of the points in a spike fall within the template, the new waveform was considered to be a match. The electrophysiological parameters of the action potential were used to identify whether the channel contained any spurious signals (e.g., electrical noise, movement artifact). Artifact signals were not classified as action potentials and were removed. The remainder of the waveforms were then examined in detail for single units. The peak-to-peak amplitude, waveform shape, and interspike intervals (ISI) were evaluated to ensure that the sorted action potentials had a characteristic and distinct shape when compared with other neuronal waveforms in the same channel.

Example 4

Longitudinal Analysis of Single Neurons

For the analysis presented herein, the activity of single neurons from CA1-2 and dentate of three animals were spike sorted. A critical component in studying neuronal activity chronically over long periods of time is the ability to specify the activity from the same unit with confidence over multiple recording sessions. We compare the average action potential waveform (computed each recording session) from six neurons over 36 days (5 sessions). To confirm that the same unit was being sampled, we performed a one-way ANOVA, with each neuron's waveshape representing a data group. The ANOVA test was repeated for each neuron to compare the waveshapes over the five recording sessions (five data groups for each neuron). The null hypothesis that the longitudinal samples come from the same group was accepted with at least 95% confidence for all but one of the neurons. We observed slight variations in the action potential tails of the remaining neuron, which resulted in a confidence level of 90%.

Qualitative analysis of the raw recordings revealed that the neuronal activity was dynamically modulating as the animals developed into the epileptic state. The aim of the single neuron analysis is to build a statistical foundation of the firing properties of the epileptogenic hippocampal neurons. The firing times of single neurons were used to quantify changes in the interspike interval (ISI) mean and standard deviation (in an 1800 second window) over recording sessions. As the animals progressed into a spontaneously seizing condition, the firing rate and number of firings increase. The increase in firing rate is measured by a decrease in interspike interval and increase in the total number of firings. The longitudinal component of the epileptogenic process of this study tracks both of the statistical neuronal firing changes in detail. As time progressed, we found that the mean ISI is linearly decreased over recording sessions. The CA1-2 neurons of a sham animal exhibited a significantly smaller change in the ISI over recording sessions (33 day duration). For example, a representative control neuron changed the mean and standard deviation of its ISI from 17.23±23.75 to 19.60±21.98, with a corresponding linear fit of the form y=−0.05±16.1. This value is an order of magnitude smaller slope that the values found for the epileptogenic animals. An overall decrease in the mean ISI value indicates that the neurons are firing more often, but this decrease is additionally coupled with a modulation in the standard deviation, which can be used as an indicator of neuronal bursting. High standard deviations are indicative of increases in bursting.

To evaluate the relationship between neuronal firing patterns, raster plots were used (FIG. 5B), in which each vertical line indicates the time a single neuron fired. Over time, it is seen that the density of vertical lines increases, which qualitatively represents an increase in firing rate. The second component of the modulation is that over time an increase is observed in the number of thick vertical lines, which indicate that the particular neuron is firing very frequently in a short time interval. The firing is so frequent that the individual firings cannot be distinguished. These marks in the raster plot represent bursts. The modulation of the example raster plots shown in FIG. 5AB shows an obvious increase in the frequency and duration of the bursting as time progressed from stimulation.

The firing patterns for the control animal were very regular with few bursting patterns. Overall, the epileptogenic animals exhibited burst/silence characteristics while the controls had more uniform activity. In summary, analysis of single unit neuronal activity suggests that on the single neuron level, there are dynamic changes in activity as indicated by the temporal variation in neuronal firing rate. The changes are marked by an increase in the amount of irregularity in the firing.

Example 5

Multiunit Analysis

The single neuron analysis provides insight to the timing relations in epileptic hippocampal neurons; however it does not consider the activity of the local ensemble of neurons surrounding the electrode tip. It is generally assumed that a degree of redundancy exists among the population and accordingly interpretations from single unit analyses can be extended to the ensemble. To address the contribution of ensembles to the epilepsy process, we present a complementary view of the evolution of neuronal activity from the ensemble potential level using the same microelectrodes of the single unit analysis. For this analysis we emphasize features of the action potential in the raw recordings but do not extract the precise firing of each of the neurons. Therefore, analysis is presented on potentials that were only bandpass filtered between 300 Hz and 6 kHz (no spikes were detected or sorted).

The potentials generated in this manner contain a much greater diversity of neuronal activity from neurons both close to and distant from the electrode tip. This analysis addresses the question of whether the same features of epileptogenesis exist at the population level when compared to the single unit analysis. From a practical standpoint, it will be appreciated that analysis on this level can decrease the complexity of spike detection and sorting for neuroprosthetic design and implementation.

We utilize the signal processing methodology of linear autoregressive (AR) modeling to quantify the local time structure of the recorded time series. The purpose of fitting AR models to the ensemble potentials is to capture within them the spectral content and spike bursting rythmicity throughout the temporal evolution of a recording session and between sessions. We have applied the AR modeling directly to the bandpass filtered CA1-2 and dentate time series segments as described above. This method prescribes windowing the signal of interest and approximating future samples as a linear combination of previous samples using the equation $$\tilde{s} = \sum_{k=1}^{p} \alpha_k s(t_N - t_{N-k})$$

where $s(t_N)$ is the original signal at sample N, $\tilde{s}(t)$ is the predicted signal, $\alpha_k$ are the predictor coefficients, and p is the prediction order.

A unique set of predictor coefficients for any given signal may be determined by minimizing the sum of the squared differences between the actual samples and the linearly predicted ones. These predictor coefficients served as the dependent variables in this study. We utilized the autocorrelation method for LPC to calculate the predictor coefficients. The Levinson-Durbin recursion was used to solve this system of equations (Yule-Walker) for $\alpha$.

FIG. 8A shows examples of the clusters of the first and second coefficients of all the AR models for CA1-2 neurons from epileptogenic animal #1. Each session's cluster consists of 200 AR models, which represent the system identification of 3000 seconds of data which is also inclusive of the segments used in the single neuron analysis. As with any AR modeling application, the appropriate choice of window size and prediction order must be evaluated. Here we chose 15 second non-overlapping windows and a prediction order of 2. The interpretation of the results presented herein is consistent with other choices of window size (5 or 30 seconds) and larger prediction orders of 3 or greater (as can be determined by the user). Referring to FIG. 8A, the distribution of model coefficients is quite distinct for each recording day. Prior to stimulation, the neuronal activity was very consistent, as indicated by the tight cluster of model coefficients with small variance located in quadrant 4 of the plot (quadrant designations for each plot are shown in the lower plot on the left of FIG. 8A). The delineation of quadrants was chosen so that all of the pre-stimulation model coefficients for all animals were contained within quadrant 4. One day post-stimulation we observed that several of the LPC models were significantly different than the baseline, suggesting that the firing activity for those particular model segments is statistically different from baseline. As time progressed, we observed an increasing density of models falling within quadrants 2 and 3.

To assess the differences in time-series segments represented by the models, we plotted the filtered waveforms from quadrant 2 (model: −1.83, 0.90), quadrant 3 (model: −1.74, 0.83), and quadrant 4 (model: −1.67, 0.80) as shown in FIG. 8B. The models in quadrant 2 are represented by large amplitude bursting activity lasting between 7 and 10 seconds. In contrast, the activity in quadrant 4 contains all low amplitude activity with a few single unit spikes. Intermediate to the activity in quadrant 2 and 4, quadrant 3 contains a mixture of 15-second duration bursting but at lower amplitude. The spread of the LPC model clusters indicates that there is a continuous spectrum of activity that spans the three extremes presented in FIG. 8B. Comparatively, the control animals did not produce any model parameters in quadrants 2 or 3 even 54 days post-surgery. For all animals, the control clusters indicate the data spectra are similar before stimulation. These studies show that as the animals move into a chronic epileptic state, the occurrence of bursting spectra increase.

Example 6

Spatial Effects of Local Microstimulation on Limbic Network Hyperexcitability in an Animal Model of MTLE This Example describes studies of microstimulation designed to spatially decrease limbic neuromodulation. Single neuron firing rates are used as a primary measure to determine the spatial effects of local microstimulation. In order to understand how the spatiotemporal organization of activity in limbic epileptic neuronal assemblies becomes destabilized, it is necessary to chronically use single/multi-unit electrophysiology monitoring techniques in vivo. By using many electrodes (e.g., 32) in an array configuration it can be determined if other neurons (pyramidal, interneurons, granule cells) in the network are affected. This translates into testing the ability to quantify the stimulation response of representative ensembles of neuronal recordings that directly relate to epileptic state.

6.1 Background. Extracellular electrophysiology is currently the tool of choice for performing high-resolution recording from neural tissue in an awake animal [B9]. It offers information about the spiking (output) and synaptic activity (input) of neurons in the recorded area. It is presently unknown in vivo how widespread chronic stimulation of the hippocampus and surrounding structures affects neuronal network activation and epileptic state as a function of the delivered stimulus. Building on established principles of neural ensemble recording and our past experience, we characterize the continuous activity of neurons in hippocampal recorded areas synchronized with behavior during the interictal and ictal periods. The approach is to first begin with expansive spatial coverage, and use knowledge gained through analysis of neuronal firing modulation to reduce and refine the targeted structures for recording.

The trisynaptic loop, shown schematically in FIG. 11, includes dentate granule cells, CA3 pyramidal neurons, CA1 pyramidal cells, and entorhinal cortex is well known for its role in generating epileptiform activity [B43]. To quantify and track the neuronal firing that results from stimulation in vivo we employ techniques to obtain large scale sampling of the hippocampal structures that are involved with epileptiform activity. We target the classic trisynaptic loop, dentate gyrus, entorhinal cortex and from our findings are motivated to track intricate interrelations throughout the hippocampus by monitoring the activity both rostral-caudal and medial-laterial [B44-46]. By focusing on these five targets we investigate the mechanism by which firing rates change in terms of afferent and efferent firing frequency. For example, CA3 firing may slow because stimulation results in dentate granule cell firing that is slower, less correlated, or weaker. It may be the case that none of the measurements made in CA3 may detect such changes, which require no real changes in the CA3 neurons themselves. Spatially, we will determine which sites produce decreased modulation in neuronal activity as a result of stimulation and test the condition and effect of loss of activation in the trisynapic loop, entorhinal cortex, and dentate gyrus.

The ability to spatially identify increased or decreased modulation in this loop will provide insight to the mechanisms of epileptic state. We are motivated to sample these structures because they contain a network of highly interconnected neurons, which have been implicated in MTLE [47, 48]. We will study within layer V of the neocortex and CA1-3 of the hippocampus, the excitatory interconnectivity of pyramidal and interneurons, the presence of intrinsically burst-generating cells, excitatory granule cells of the dentate gyrus, and the changes in activity that result from microstimulation. We hypothesize that the neurons with the largest diameters will be most affected by stimulation however the intensity of stimulation can also impact interneurons. The details of how the selection of parameters chronically activates the neurons are described in section 3.2.

6.2 Experimental Design.

6.2.1 Animal electrophysiological recordings. Fifty day-old adult male Sprague-Dawley rats are premedicated with xylazine and then anesthetized with isoflurane in oxygen and placed in a Kopf stereotactic frame. A midline incision is made in the scalp and all soft tissue is loosened from the dorsum of the skull. A craniotomy is drilled (and dura removed) for electrode placement such that the long axis of a 2×8 array can extend A-P, M-L, or on a diagonal from midline. A total of 32 microwire recording electrodes are chronically implanted into the limbic system as illustrated in FIG. 12. These recording sites are chosen because of their role in the generation of epileptic discharges [B49]. Electrophysiological and auditory cues generated from surgical recordings are used to intraoperatively verify electrode placement endpoints and the identification of pyramidal and interneurons. Each electrode array consists of 50 µm (or smaller) polyimide insulated tungsten microwires with 200 µm separation (or smaller) within electrodes. A bipolar twisted Teflon-sheathed stainless steel 330 µm diameter electrode is implanted in the contralateral posterior ventral hippocampus for stimulation into status epilepticus as described [B7]. All electrodes are chronically secured with dental cement and anchored to four micro screws driven into the bone of the skull.

One week following surgery, the bipolar twist electrodes are used to induce self-sustained limbic status epilepticus. A suprathreshold stimulus of 240 µA is delivered for 60 minutes using 10 sec trains of 50 Hz 1 ms (duty cycle) bipolar square waves every 12 seconds. Once spontaneous seizures develop, the severity of seizures is graded. A behavioral seizure score (BSS) is determined using the standard Racine scale (0, no change; 1, wet dog shakes; 2, head bobbing; 3, forelimb clonus; 4, forelimb clonus and rearing; 5, rearing and falling).

6.2.2 Data handling. In concert with the spatial sampling, we continue to record and store the data across all channels at least with at minimum of 12 kHz of sampling rate to maintain the ability to discriminate the activity of single neurons. Included in the microelectrode recording technique is access to local field potentials (LFP—0.1-100 Hz) which represent dendritic neuronal input and the action potentials of neuronal output (300-6 kHz).

6.2.3 Stimulation methods and settings. Stimulation induced neuromodulation testing sessions are conducted using a Tucker-Davis RX7 Stimulus isolator system. Initial selection of stimulation parameters is based on the preliminary measurements that indicate the points of maximal excitation and inhibition, to limit the number of stimulus combinations in the study of the spatial effects network hyperexcitability. Those of skill in the art will appreciate that these stimulation settings can change in an epileptic animal and therefore firing rates are concurrently monitored to provide points of reference.

The initial selected settings can be chosen from the peaks of studies as described above and illustrated in FIG. 10B, and e.g., can include stimulation parameters such as the following: (0.3 Hz, 10 s.), (3 Hz, 5 s.), (30 Hz, 10 s), (130 Hz, 1 s), and (300 Hz, 5 s). Each stimulation setting is randomly repeated, e.g., three times (at an intensity of 10, 50, and 100 µA) during each recording session. The protocol is repeated, preferably daily.

Microstimulation pulse trains can consist of cathodic first, charge-balanced, biphasic square-wave pulses (2 ms pulse: width) delivered at 100 µA [B50]. These stimulation frequencies, duration, and intensity are suitable because of their use in DBS and VNS therapies [B20, B51]. The current spread for the intensity of stimulation as described in this Example is computed to be 150 µm [B21, B22].

6.2.4 Quantifying stimulus-modulated bursting and statistical validation with sham animals. Studies described herein show that neuronal bursting plays a role in supporting epileptic spiking activity; therefore, it is desirable to systematically evaluate the spatial characteristics of the burst response to stimulation on both the neuronal and ensemble level. The micro-level data is useful for identifying those neurons that are destabilizing, and indicating when the destabilization occurs. The administration of the stimulation at the prescribed settings (in the section above) will be triggered by the identification of a neuronal burst using a protocol for temporal quantification of bursting is described below.

Closed-loop responsive stimulation in response to abnormal electrographic discharges has been studied in the clinical setting for several years [B52]. In trials in which electrical stimulations were applied to the cortex for functional mapping, responsive cortical electrical stimulation in response to epileptic activity has been shown to shorten afterdischarges, or even abort seizures [B53-B55]. Accordingly, burst-triggered stimulation is expected to be a valuable therapy for intervention on the microscopic level. Temporal quantification of bursts in neuronal activity can be either considered to be discrete events with modulating amplitudes, or single spikes with short within-burst interspike intervals. While these two criteria are sufficient to identify typical examples, it is difficult to quantitatively identify the bursting modulation. In vivo bursts have been observed in different forms in a variety of normal and epileptic states [B34, B35, B38, B56, B57]. Therefore, it is important to account for the size of bursts, measured in terms of number of participating neurons, aggregate number of spikes, amplitude, or duration [B36] in both normal and epileptic individuals. To establish a baseline in the statistics of bursting, at least five sham animals are implanted with microwire arrays in the same anatomical areas as the described animal model of TLE. The bursting nature of the neuronal network is quantified during the states of sleeping, quiet exploration, and higher activity. All subsequent analysis in epileptic individuals is referred back to the data from sham animals and is tested for statistical differences.

Burst discharges are typically characterized by intraburst spikes and 4-10 msec intraburst interspike intervals [B37] whereas interburst intervals of spontaneously bursting cells of interest, e.g., pyramidal cells, can vary from seconds to minutes [B58]. For the majority of the neurons it is expected that the probability of observing n spikes in a burst will decrease exponentially with n while neurons that exhibit long bursts will decrease supraexponentially with n [B37]. Long temporal averages (hours) are used in deriving statistical metrics to reduce the effect of noise.

An object of the invention is to elucidate the underlying organizational properties of intra-hippocampal bursting that result from stimulation during the interictal and ictal periods. Statistical and computational knowledge in this area is useful for specifying "where" in the array to stimulate and "how often" to stimulate the abnormal hippocampal bursting system. Moreover, determination of the functional recruitment in abnormal hippocampal bursting activity is predicted to enhance understanding of modifications of the spatial pathways involved in the interictal/ictal transition.

6.2.5 Computing fraction of synchronous firing across electrodes over time. The burst detection strategies described above are used to create a discrete set of spatio-temporal events. From this matrix of values, statistics regarding the fraction of synchronous firing from CA1-3, dentate, entohrinal cortex, and the electrode array as a whole can be built. The fraction is monitored and compared both within a session and longitudinally interictally and is used to determine where synchrony is originating and if it is dominating the hippocampus over time.

6.2.6 Developing probabilistic burst chains. The fine-timing relationships in the bursting matrix are quantified by computing a multi-class probability distribution among successive bursting times. For example, one can compute the probability of dentate bursting given CA1-3 bursting, CA1-3 bursting given dentate bursting, CA1-3 bursting given CA1-3 bursting, and dentate bursting given entohrinal cortex bursting. This statistical quantification provides insight into the functional connectivity within the bursting hippocampus. More specifically, this type of analysis can determine if the dentate, entohrinal cortex, or CA1-3 is leading or lagging the bursting, in addition to quantifying which region has the highest probability of bursting.

6.2.7 Estimating animal numbers. To determine the statistical significance of the data generated herein, we performed a power analysis for the number of animals. While the basis for an appropriate selection of animal numbers depends largely on the nature of the study itself, we consider the firing properties of the normal and abnormal neural networks to be the variables of interest. It is assumed that the interspike intervals from microstimulated animals is significantly different from control animals. The null hypothesis is that the mean of the two groups is the same. We implemented the t-test using Welch's approximation for the degrees of freedom. Referring to sample data describe above, we obtained the following calculation. If we assume that for an epileptic animal the average interspike interval over time is $3.16\pm21.28$ and the average ISI for a normal animal is $17.23\pm23.75$, then to achieve 95% confidence that the animals are not from the same population we need 56 animals. Such a calculation can be used to estimate the number of animal models with high quality simultaneous stimulated single unit recording that can be produced showing the desired behavior. Additionally, it is prudent to plan for an estimated 25% premature mortality rate.

6.2.8 Alternative experimental approaches. The stimulation processes may result in electrochemical oxidation and reduction reactions including gas evolution (hydrogen evolution at the cathode, oxygen and chlorine evolution at the anode), in the surrounding tissue [B59]. If such a problem is encountered during stimulation, biphasic stimulation can be used to balance the effects of anodic and cathodic electrode reactions in the vicinity of the electrode.

Despite the attractiveness of the CLE model as described above, the spontaneous seizures that occur in this model are unpredictable in their frequency. For this reason, the test animals are maintained under continuous video/electrophysiological recording Degrees of Freedom. The number of variables of stimulation and anatomical targeting are large compared to the goal of therapeutic effect (reducing seizure frequency and duration). Instead of exploring all of the combinations we are electing to study the most common settings (frequency, pulse width, duration) employed in the clinic that have produced 'responders' and the specific settings that have produced maximal and minimal excitation/inhibition in our preliminary studies.

A minor problem that may be encountered during long-term monitoring is the interruption or premature termination of longitudinal video-EEG data caused by the unexpected loss of an animal's electrode headset, which can generally be avoided with adequate techniques for securing the headset, such as a clamp in the craniotomy.

Loss of single neuron recording. Chronic microelectrode technology, at the post-surgical stage, is subject to changes in the extracellular environment. Therefore, the viability of chronic electrodes and recording from single neurons has been limited to times from a few months to a year [B60]. We have developed techniques to contend with the complications that can result from chronic array implantation [B61] and we have successfully recorded single neurons in rats for up to one year. Furthermore, many informative studies can be conducted in periods of less than one year.

Example 7

Determining Chronic Temporal Cellular Effects of Microstimulation on Limbic Neuronal Hyperexcitability in an Animal Model of MTLE This Example describes methods and approaches appropriate to demonstrate that microstimulation has lasting molecular effects measurable by in vivo electrophysiology and can provide an assessment of the normal and epileptic state, as well as how stimulation can modify hyperexcitability temporally.

7.1. Background. Presently there are few guidelines for the selection of stimulus parameters that chronically limit limbic neuronal hyperexcitability. While the mechanisms of action of chronic microstimulation are believed to closely mimic the effects of a lesion, they could potentially involve disruption (through signal mixing making the outgoing neuronal interaction unable to sustain oscillatory activity) of the synchronizing signal, neuronal silencing, as well as axon stimulation. Moreover, it is possible that the mechanisms interact separately or combined to achieve the effect, which may include suppression of firing (due to membrane interactions or synaptic inhibition, e.g. GABAergic neurons). This is related to specific inactivation of calcium and sodium voltage dependent channels.

Stimulus parameters can be used to control selectively which neural elements in the surrounding tissue are excited. The stimulus parameters can also control the spatial extent of neural elements that are excited. Finding the optimal setting is complicated because for epilepsy, it is currently unknown which neural elements are excited with stimulation. It is therefore important to develop an increased understanding of the fundamentals of electrical stimulation of the limbic system to make rational and informed choices in setting stimulus parameters.

The main components involved in the tissue-stimulus interactions [B62] are the following:

a) Excitation-pulse width relationship. The stimulus current required to excite neural elements decreases as pulse width increases and is governed by Weiss Equation. Theoretical studies indicate that short pulse durations increase the threshold difference between activation of different diameter nerve fibers [B63] and between activation of nerve fibers lying at different distances from the electrode [B64].

b) Charge-duration relationship. The rise in threshold charge with increasing pulse widths is due to accommodation, the nonlinear time-dependent conductance properties of ion channels in the neural membrane. Short pulse widths require high current but low charge, and are thus more efficient at exciting neural elements.

c) Charge and charge density relationship. Charge density is defined as the charge divided by the geometric surface area of the electrode and is an important stimulation parameter to consider when determining the threshold and severity of tissue damage.

d) Amplitude-distance relationship. The stimulus amplitude required to activate neural elements depends on the distance between the electrode and the neuron [B65]. There exists a nonlinear relationship between the stimulus amplitude required to stimulate neural elements and distance.

e) Frequency-excitation relationship. The effect of stimulation pulse frequency has produced the most varied neuronal responses. A large range (60-1000 Hz) of frequencies has been reported to be effective at relieving symptoms. In some cases, the inhibitory effects rose linearly with increasing frequency while conversely other reports conclude that there are nonlinear changes in excitability above 130 Hz.

7.2 Experimental Design and Methods.

One approach to determining the parameters that chronically reduce epileptic network hyperexcitability is to scan all possible combinations until the desired reduction in seizure frequency and duration are obtained. The feasibility of such an approach is limited due to the large number of possible combinations. Rather we submit that in depth study of the cellular mechanisms of action for the chronic application of a reduced set of stimulation settings that decrease network hyperexcitability is an appropriate approach, with the goal of fixing a set of parameters and tracking cell modulation over time among stimulated and non-stimulated animals.

7.2.1 Electrophysiological baseline—classical neuromodulation descriptors. Results described above show that both neuronal spike detection and spike sorting methodologies enable statistical quantification of the irregularity in activity linked to individual neurons over a longitudinal study. Neuronal firing rates express excitability and therefore are a straightforward feature for directly relating the effects of stimulation to normal and abnormal brain physiology. Therefore our focus is on analysis tools that maintain the most direct relationship between the stimulus setting, epilepsy state, and neurophysiology. It is well known that neuronal firing rates can change drastically in the population depending upon the stimulation parameters. Therefore, without knowing the history of each neuron's activity it would difficult to conclude how the physiologic change is related to the epileptic state. It is the change from baseline at the level of the single neuron and the ensemble that provides contrast in the electrophysiologic states. The degree of single unit bursting has yet to be unified with traditional global and dynamical measures of epileptic state; nevertheless we believe that neuronal analysis of this type provides a fundamental approach grounded in the basics of electrophysiology.

7.2.2 Coefficient of variation (neuron level). Modulations in single neuron firing over long periods of time (days) is evaluated with the coefficient of variation (CV). The CV, which is the ratio of ISI standard deviation to mean value, is a commonly used alternative measure to assess the amount of irregularity in neuronal firing [B66]. Threshold and template based spike detection is implemented to determine the firings of single neurons. Upon computing the interspike interval mean and standard deviation, the CV is computed in real-time using window based statistics. Lower values of the CV indicate periodicity in firing, and higher values tend toward bursting activity [B67, B68]; therefore detection of CV values 2 standard deviations above the mean are useful to determine bursting.

7.2.3 Signal integration (neuron or ensemble level). Individual neuronal activity is monitored at each electrode in real time to provide single and multiunit spike information over long durations (e.g., days). Due to the complex nature of spiking bursts, either bin rates of single unit activity or signal integration of the raw potentials are used for feature extraction. For these studies the integration constant can be set, e.g., at 100 ms, and two thresholds can be used to define the integrated burst profiles. The low threshold is used to eliminate small groups of bursting whereas the second threshold is used to determine acceptance of a burst. In cases of both binning and population integration, a running total of burst duration and frequency is tallied.

7.2.4 Interburst interval histograms among CA1-3 and dentate. The frequency of intra-hippocampal bursting is determined by computing interburst interval histograms for each of the electrodes in the burst matrix. The peak of the histogram is tracked within sessions and longitudinally. The bursting histograms are used to provide an indication of how frequently intervention needs to be delivered to each region of the hippocampus.

Example 8

Pre-Clinical Testing of Therapeutic Efficacy of Chronic Closed-Loop Microstimulation This Example describes an efficacy trial using a double-blind, randomized, controlled pre-clinical animal protocol to be used as a prelude to human clinical trials. Components of the trial test the ability of microstimulation to reduce the frequency and duration of seizures while monitoring side effects in the animal model. Neurophysiological predictors of responsiveness, determined; by methods as described above are tested for translation as "clinical" responders. Animals that do not respond to treatment provide a corresponding neurophysiological dataset useful for expressing the results in terms of neuronal firing rates. In this Example, two groups of animals are used for recording and analysis: (epileptic+electrodes+stimulation) and (epileptic+electrodes+no stimulation), with the goal of comparing the functional differences in the two groups in terms of seizure reduction as further described below.

8.1 Trial design. Double-blind, randomized, placebo-control, two-arm parallel trial with a 1:1 randomization ratio. Prospective CLE rats undergo continuous EEG/video monitoring to confirm the presence of seizures. Doses of the stimulation trial are based upon the findings that reduce hyperexcitability as described above. In a suitable protocol, animals receive neuronal burst triggered stimulation on day 1 and stimulation on days 2 through 10. If a rat experiences intolerable adverse effects, the dose is reduced by 50% at either dosing period. Minimal doses that produce maximal efficacy are desirable, inter alia for maximizing battery life. Seizure frequency is monitored continuously as described above through direct observation and EEG monitoring. Seizures are recorded beginning on day 1. The therapeutic effect of burst triggered stimulation is compared to placebo and animals that receive stimulation randomly.

8.2 Behavioral monitoring. The preictal and ictal periods in the animal model are monitored using a video apparatus. The behavioral state is classified as either sleeping, quiet exploration, or active. Once spontaneous seizures develop, the severity of seizures is graded. A behavioral seizure score (BSS) is determined for the individuals using the standard Racine scale. The operant definition of the seizure and the EEG seizure duration is determined, as well as whether the seizure can be characterized by a low amplitude hypersynchronous fast beta activity that evolves to higher amplitude polyspike alpha waves followed by spike and wave theta activity and a postictal spike wave delta.

8.3 Efficacy analysis. The primary efficacy variables are determined by the total seizure frequency, seizure duration, and seizure grade (1-5 on a Racine scale) as defined as all seizures with or without secondary generalization. The primary endpoints are defined as a 50% reduction in any of the efficacy variables. Statistical analyses are performed on an intent-to-treat model. A secondary efficacy variable is the total partial seizure frequency per 9 days during the double-blind treatment phase. This variable is analyzed using the Wilcoxon rank-sum test on the ranks of the partial seizure frequency per 9 days. The total partial seizure frequency per 9 days is computed for each rat by multiplying the daily average seizure rate of the double-blind treatment phase (starting at 8:00 AM on day 2 and ending at 8:00 AM on the morning after day 10, or at time of exit) by 9 days. Finally, total partial seizures evolving to secondarily generalized seizures per 9 days are evaluated by treatment group; The sample size is based on the efficacy variables as relevant information for the calculation based on the primary efficacy variable for the rat population.

REFERENCES

It is believed that a review of the references will increase appreciation of the present invention. The entire disclosures of all references cited herein are hereby incorporated by reference. All publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention. The disclosures of all references cited herein are incorporated herein by reference.

Some of the following documents are referred to throughout the present disclosure by a number, or by a letter and a number in brackets, as indicated below

[1] L. D. Iasemidis, "Epileptic Seizure Prediction and Control," *IEEE Transations on Biomedical Engineering*, vol. 50, pp. 549-558, 2003.

[2] L. D. Iasemidis, K. Pappas, R. Gilmore, S. Roper, and J. Sackellares, "Preictal Entrainment of a Critical Cortical Mass is a Necessary Condition for Seizure Occurrence," *Epilepsia*, vol. 37, 1996.

[3] M. Le Van Quyen, J. Martinerie, V. Navarro, P. Boon, M. D'Have, C. Adam, B. Renault, F. Varela, and M. Baulac, "Anticipation of Epileptic Seizures from Standard EEG Recordings," *The Lancet*, vol. 357, pp. 183, 2001.

[4] K. Lehnertz and C. Elger, "Can Epileptic Seizures be Predicted? Evidence from Nonlinear Time Series Analysis of Brain Electrical Activity," *Physical Review Letters*, vol. 80, pp. 5019-5022, 1998.

[5] B. Litt, R. Esteller, J. Echauz, M. D'Alessandro, R. Shor, T. Henry, P. Pennell, C. Epstein, R. Bakay, M. Dichter, and G. Vachtsevanos, "Epileptic Seizures May Begin Hours in Advance of Clinical Onset: A Report of 5 Patients," *Neuron*, vol. 29, pp. 51-64, 2001.

[6] I. Osorio, M. G. Frei, J. Giftakis, and T. Peters, "Performance Reassessment of a Real-Time Seizure Detection Algorithm on Long ECoG Series," *Epilepsia*, vol. 43, pp. 1522-1535, 2002.

[7] N. D. Schiff, D. R. Labar, and J. D. Victor, "Common Dynamics in Temporal Lobe Seizures and Absence Seizures," *Neuroscience*, vol. 91, pp. 417-428, 1999.

[8] A. Bragin, J. Csicsvari, M. Penttonen, and G. Buzsaki, "Epileptic Afterdischarge in the Hippocampal-Entorhinal System: Current Source Density and Unit Studies," *Neuroscience*, vol. 76, pp. 1187-1203, 1997.

[9] R. D. Traub and R. K. Wong, "Cellular Mechanism of Neuronal Synchronization in Epilepsy," *Science*, vol. 216, pp. 745-747, 1982.

[10] D. H. Johnson, "Point Process Models of Single-Neuron Discharges," *Journal of Computational Neuroscience*, vol. 3, pp. 275-299, 1996.

[11] A. Knoblauch and G. Palm, "What is Signal and What is Noise in the Brain?" *BioSystems*, vol. 79, pp. 83-90, 2005.

[12] W. R. Sofiky and C. Koch, "The Highly Irregular Firing of Cortical Cells is Inconsistent with Temporal Integration of Random EPSPs," *The Journal of Neuroscience*, vol. 13, pp. 334-350, 1993.

[13] J. F. Kaiser, "On a simple algorithm to calculate "energy of a signal," Proceedings of ICASSP, 1990.

[14] H. P. Zaveri, W. J. Williams, and J. C. Sackellares, "Energy based detection of Seizures," presented at Annual International Conference of the IEEE Engineering in Medicine and Biology Society, 1993.

[15] L. R. Rabiner and B. H. Juang, *Fundamentals of speech recognition*. Englewood Cliffs, N.J.: PTR Prentice Hall, 1993.

[16] X. D. Huang, Y. Ariki, and M. A. Jack, *Hidden Markov Models for Speech Recognition*. Edinburgh Univ. Press, 1990.

[17] Y. Linde, A. Buzo, and R. M. Gray, "An Algorithm for Vector Quantizer Design," *IEEE Transations on Communication*, vol. 28, pp. 84-95, 1980.

[18] R. L. Rabiner and R. W. Schafer, *Digital Processing of Speech Signals*. Englewood Cliffs: Prentice-Hall, 1978.

[19] S. S. Haykin, *Neural networks: a comprehensive foundation*, 2nd ed. Upper Saddle River, N.J.: Prentice Hall, 1999.

[20] J. C. Principe, N. R. Euliano, and W. C. Lefebvre, "Neural and adaptive systems: fundamentals through simulations." New York: Wiley, 2000.

[21] J. C. Sanchez, D. Erdogmus, Y. Rao, K. E. Hild, J. Wessberg, M. Nicolelis, and J. C. Principe, "A Model Based Approach to Quantify Motor Cortical Neuronal Interactions in a Brain Machine Interface," *Neural Computation*, vol. Submitted, 2003.

[22] J. H. Goodman, R. E. Berger, and T. K. Tcheng, "Preemptive Low-frequency Stimulation Decreases the Incidence of Armygdala-kindled Seizures," *Epilepsia*, vol. 46, pp. 1-7, 2005.

[23] K. A. Richardson, B. J. Gluckman, S. L. Weinstein, C. E. Glosch, J. B. Moon, R. P. Gwinn, K. Gale, and S. J. Schiff, "In vivo modulation of hippocampal epileptiform activity with radial electric fields," *Epilepsia*, vol. 44, pp. 768-777, 2003.

[24] F. A. Lado, L. Velisek, and S. L. Moshe, "The effect of electrical stimulation of the subthalamic nucleus on seizures is frequency dependent," *Epilepsia*, vol. 44, pp. 157-164, 2003.

[25] E. E. Fanselow, A. P. Reid, and M. A. Nicolelis, "Reduction of pentylenetetrazole-induced seizure activity in awake rats by seizure-triggered trigeminal nerve stimulation," *Journal of Neuroscience*, vol. 20, pp. 8160-8168, 2000.

[26] S. Xu, S. K. Talwar, E. S. Hawley, L. L., and J. K. Chapin, "A multi-channel telemetry system for brain microstimulation in freely roaming animals," *Journal of Neuroscience Methods*, vol. 133, pp. 57-63, 2004.

[27] J. W. Gnadt, S. D. Echols, A. Yildirim, H. Zhang, and K. Paul, "Spectral Cancellaton of Microstimulation Artifact for Simultaneous Neural Recording In Situ," *IEEE Transitions on Biomedical Engineering*, vol. 50, pp. 1129-1135, 2003.

[28] Stables, J. P., et al., Models for epilepsy and epileptogenesis: Report from the NIH Workshop, Bethesda, Md. Epilepsia, 2002. 43(11): p. 1410-1420.

[29] M. B. Zugaro et al., "Spike Phase Precession Persists after Transient Intrahippocampal Perturbation", *Nature Neuroscience*, vol. 8(1)67-71, 2005.

[30] K. Kaneda, Y. Fujiwara-Tsukamoto, et al. (2005). "Region-specific modulation of electrically induced synchronous oscillations in the rat hippocampus and cerebral cortex." Neuroscience Research 52(1): 83.

[31] B. B. Averbeck and D. Lee (2004). "Coding and Transmission of Information by Neural Ensembles," *Trends in Neurosciences* 27(4):225-230.

[B1] J. C. Sanchez, T. H. Mareci, W. M. Norman, J. C. Principe, W. L. Ditto, and P. R. Carney, "Evolving into Epilepsy: Multiscale Electrophysiological Analysis and Imaging in an Animal Model," *Experimental Neurology*, vol. 198, pp. 31-47, 2006.

[B2] E. H. Bertram and J. Cornett, "The ontogeny of seizures in a rat model of limbic epilepsy: evidence for a kindling process in the development of chronic spontaneous seizures," *Brain Research*, vol. 625, pp. 295-300, 1993.

[B3] E. H. Bertram and J. F. Cornett, "The Evolution of a Rat Model of Chronic Spontaneous Limbic Seizures," *Brain Research*, vol. 661, pp. 157-162, 1994.

[B4] E. H. Bertram and E. W. Lothman, "Morphometric Effects of Intermittent Kindled Seizures and Limbic Status Epilepticus in the Dentate Gyrus of the Rat," *Brain Research*, vol. 603, pp. 25-31, 1993.

[B5] M. Quigg, E. H. Bertram, and T. Jackson, "Longitudinal distribution of hippocampal atrophy in mesial temporal lobe epilepsy," *Epilepsy Research*, vol. 27, pp. 101-110, 1997.

[B6] M. Quigg, M. Straume, M. Menaker, and E. H. Bertram, "Temporal distribution of partial seizures: comparison of an animal model with human partial epilepsy," *Ann Neurol*, vol. 43, pp. 748-755, 1998.

[B7] E. W. Lothman, E. H. Bertram, J. Kapur, and J. L. Stringer, "Recurrent Spontaneous Hippocampal Seizures in the Rat as a Chronic Sequela to Limbic Status Epilepticus," *Epilepsy Research*, vol. 6, pp. 110-118, 1990.

[B8] E. W. Lothman, D. A. Rempe, and P. S. Mangan, "Changes in Excitatory Neurotransmission in the Ca1 Region and Dentate Gyrus in a Chronic Model of Temporal-Lobe Epilepsy," *Journal of Neurophysiology*, vol. 74, pp. 841-848, 1995.

[B9] M. A. L. Nicolelis, *Methods for Neural Ensemble Recordings*. Boca Raton: CRC Press, 1999.

[B10] M. S. Lewicki, "A review of methods for spike sorting: the detection and classification of neural action potentials," *Network: Computation in Neural Systems*, vol. 9, 1998.

[B11] J. K. Chapin, "Using multi-neuron population recordings for neural prosthetics," *Nature Neuroscience*, pp. 452-455, 2004.

[B12] G. Buzsaki, "Large-scale recording of neuronal ensembles," *Nature Neuroscience*, pp. 446-451, 2004.

[B13] E. Zrenner, "Will Retinal Implants Restore Vision?," *Science*, vol. 295, pp. 1022-1025, 2002.

[B14] E. E. Fetz and D. V. Finocchio, "Correlations between activity of motor cortex cells and arm muscles during operantly conditioned response patterns," *Exp Brain Res*, vol. 23, pp. 217-240, 1975.

[B15] G. E. Loeb, "Cochlear Prosthetics," *Annual Review Of Neuroscience*, vol. 13, pp. 357-371, 1990.

[B16] M. M. Mersenich, "Coding of Sound in a Cochlear Prosthesis: Some Theoretical and Practical Considerations," *Ann NY Acad Sci*, vol. 405, 1983.

[B17] M. R. Delong, "Primate Models of Movement-Disorders of Basal Ganglia Origin," *Trends in Neurosciences*, vol. 13, pp. 281-285, July 1990.

[B18] J. Csicsvari, H. Hirase, A. Czurko, A. Mamiya, and G. Buzsaki, "Oscillatory coupling of hippocampal pyramidal cells and interneurons in the behaving rat," *Journal of Neuroscience*, vol. 19, pp. 274-287, 1999.

[B19] T. Klausberger, P. J. Magill, L. F. Marton, J. D. B. Roberts, P. M. Cobden, G. Buzsaki, and P. Somogyi, "Brain-state- and cell-type-specific firing of hippocampal interneurons in vivo," *Nature*, vol. 421, p. 844, 2003.

[B20] W. H. Theodore and R. S. Fisher, "Brain stimulation for epilepsy," *The Lancet Neurology*, vol. 3, p. 111, 2004.

[B21] P. L. Nunez, *Electric Fields of the Brain: The Neurophysics of EEG*. New York: Oxford University Press, 1981.

[B22] S. D. Stoney, W. D. Thompson, and H. Asanuma, "Excitation of pyramidal tract cells by intracortical stimulation: effective extent of stimulating current," *J. Neurophysiol.*, vol. 31, pp. 659-669, 1968.

[B23] L. D. Iasemidis, "Epileptic Seizure Prediction and Control," *IEEE Transations on Biomedical Engineering*, vol. 50, pp. 549-558, 2003.

[B24] L. D. Iasemidis, K. Pappas, R. Gilmore, S. Roper, and J. Sackellares, "Preictal Entrainment of a Critical Cortical Mass is a Necessary Condition for Seizure Occurrence," *Epilepsia*, vol. 37, 1996.

[B25] M. Le Van Quyen, J. Martinerie, V. Navarro, P. Boon, M. D'Have, C. Adam, B. Renault, F. Varela, and M. Baulac, "Anticipation of Epileptic Seizures from Standard EEG Recordings," *The Lancet*, vol. 357, p. 183, 2001.

[B26] K. Lehnertz and C. Elger, "Can Epileptic Seizures be Predicted? Evidence from Nonlinear Time Series Analysis of Brain Electrical Activity," *Physical Review Letters*, vol. 80, pp. 5019-5022, 1998.

[B27] B. Litt, R. Esteller, J. Echauz, M. D'Alessandro, R. Shor, T. Henry, P. Pennell, C. Epstein, R. Bakay, M. Dichter, and G. Vachtsevanos, "Epileptic Seizures May Begin Hours in Advance of Clinical Onset: A Report of 5 Patients," *Neuron*, vol. 29, pp. 51-64, 2001.

[B28] I. Osorio, M. G. Frei, J. Giftakis, and T. Peters, "Performance Reassessment of a Real-Time Seizure Detection Algorithm on Long ECoG Series," *Epilepsia*, vol. 43, pp. 1522-1535, 2002.

[B29] N. D. Schiff, D. R. Labar, and J. D. Victor, "Common Dynamics in Temporal Lobe Seizures and Absence Seizures," *Neuroscience*, vol. 91, pp. 417-428, 1999.

[B30] A. Bragin, J. Csicsvari, M. Penttonen, and G. Buzsaki, "Epileptic Afterdischarge in the Hippocampal-Entorhinal System: Current Source Density and Unit Studies," *Neuroscience*, vol. 76, pp. 1187-1203, 1997.

[B31] R. D. Traub and R. K. Wong, "Cellular Mechanism of Neuronal Synchronization in Epilepsy," *Science*, vol. 216, pp. 745-747, 1982.

[B32] H. Khosravani, P. L. Carlen, and J. L. P. Velazquez, "The Control of Seizure-Like Activity in the Rat Hippocampal Slice," *Biophysical Journal*, vol. 84, pp. 687-695, 2003.

[B33] M. Isokawa-Akesson, C. L. Wilson, and T. L. Babb, "Structurally Stable Burst and Synchronized Firing in Human Amygdala Neurons: Auto- and Cross-Correlation Analyses in Temporal Lobe Epilepsy," *Epilepsy Research*, vol. 1, pp. 17-34, 1987.

[B34] A. E. Telfeian, H. J. Federoff, P. Leone, M. J. During, and A. Williamson, "Overexpression of GluR6 in rat hippocampus produces seizures and spontaneous nonsynaptic bursting in vitro," *Neurobiology Of Disease*, pp. 362-374, 2000.

[B35] M. W. Slutzky, P. Cvitanovic, and D. J. Mogul, "Manipulating Epileptiform bursting in the rat hippocampus using chaos control and adaptive techniques," *Ieee Transactions On Biomedical Engineering*, pp. 559-570, 2003.

[B36] D. A. Wagenaar, R. Madhavan, J. Pine, and S. M. Potter, "Controlling bursting in cortical cultures with closed-loop multi-electrode stimulation," *Journal Of Neuroscience*, pp. 680-688, 2005.

[B37] K. D. Harris, H. Hirase, X. Leinekugel, D. A. Henze, and G. Buzsaki, "Temporal interaction between single spikes and complex spike bursts in hippocampal pyramidal cells," *Neuron*, pp. 141-149, 2001.

[B38] G. Buzsaki, J. Csicsvari, G. Dragoi, K. Harris, D. Henze, and H. Hirase, "Homeostatic maintenance of neuronal excitability by burst discharges in vivo," *Cerebral Cortex*, pp. 893-899, 2002.

[B39] G. C. Teskey and R. J. Racine, "Increased Spontaneous Unit Discharge Rates Following Electrical Kindling in the Rat," *Brain Research*, vol. 624, pp. 11-8, 1993.

[B40] F. Kloosterman, T. van Haeften, and F. H. Lopes da Silva, "Two Reentrant Pathways in the Hippocampal-Entorhinal System," *Hippocampus*, vol. 14, pp. 1026-1039, 2004.

[B41] J. Markel and A. Gray, *Linear Prediction of Speech*. New York: Springer-Verlag, 1976.

[B42] D. A. McCormick and D. Contreras, "On the cellular and network bases of epileptic seizures," *Annual Review Of Physiology*, pp. 815-846, 2001.

[B43] G. Avanzini and S. Franceschetti, "Cellular biology of epileptogenesis," *Lancet Neurology*, pp. 33-42, 2003.

[B44] P. R. Carney, M. F. Maze, D. S. Shiau, A. Srivastiva, L. D. Iasemidis, P. M. Pardalos, and J. C. Sackellares, "State-specific nonlinear neurodynamic features in an animal model of generalized epilepsy," *Epilepsia*, vol. 43, p. 270, 2002.

[B45] P. R. Carney, S. P. Nair, L. D. Iasemidis, D. S. Shiau, P. M. Pardalos, D. Shenk, W. M. Norman, and J. C. Sackellares, "Quantitative analysis of EEG in the rat limbic epilepsy model," *Neurology*, vol. 62, pp. A282-A283, 2004.

[B46] P. R. Carney, D. S. Shiau, P. M. Pardalos, L. D. Iasemidis, W. Chaovalitwongse, and J. C. Sackellares, "Nonlinear neurodynamical features in an animal model of generalized epilepsy" in *Quantitative Neuroscience: Models, Algorithms, Diagnostics, and Therapeutic Applications* New York: Kluver Academic Publishers, 2004, pp. 37-52.

[B47] F. Bartolomei, I. Bosma, M. Mein, J. C. Baayen, J. C. Reijneveld, T. J. Postma, J. J. Heimans, B. W. van Dijk, J. C. de Munck, A. de Jongh, K. S. Cover, and C. J. Stam, "How do brain tumors alter functional connectivity? A magnetoencephalography study," *Annals Of Neurology*, pp. 128-138, 2005.

[B48] A. Bragin, C. L. Wilson, and J. Engel, "Chronic epileptogenesis requires development of a network of pathologically interconnected neuron clusters: A hypothesis," *Epilepsia*, pp. S144-S152, 2000.

[B49] K. Kaneda, Y. Fujiwara-Tsukamoto, Y. Isomura, and M. Takada, "Region-specific modulation of electrically induced synchronous oscillations in the rat hippocampus and cerebral cortex," *Neuroscience Research*, vol. 52, p. 83, 2005.

[B50] Y. Temel, V. Visser-Vandewalle, M. van der Wolf, G. H. Spincemaille, L. Desbonnet, G. Hoogland, and H. W. M. Steinbusch, "Monopolar versus bipolar high frequency stimulation in the rat subthalamic nucleus: differences in histological damage," *Neuroscience Letters*, vol. 367, p. 92, 2004.

[B51] A. Handforth, C. M. DeGiorgio, and S. C. Schachter, "Vagus nerve stimulation therapy for partial-onset seizures: a randomized active-control trial," *Neurology*, vol. 51, pp. 48-55, 1998.

[B52] M. Morrell, "Brain stimulation for epilepsy: can scheduled or responsive neurostimulation stop seizures?," *Current Opinion In Neurology*, vol. 19, pp. 164-168, April 2006.

[B53] R. P. Lesser, S. H. Kim, L. Beyderman, D. L. Miglioretti, W. R. S. Webber, M. Bare, B. Cysyk, G. Krauss, and B. Gordon, "Brief bursts of pulse stimulation terminate afterdischarges caused by cortical stimulation," *Neurology*, vol. 53, pp. 2073-2081, Dec. 10, 1999.

[B54] G. K. Motamedi, R. P. Lesser, D. L. Miglioretti, Y. Mizuno-Matsumoto, B. Gordon, W. R. S. Webber, D. C. Jackson, J. P. Sepkuty, and N. E. Crone, "Optimizing parameters for terminating cortical afterdischarges with pulse stimulation (vol 43, pg 836, 2002)," *Epilepsia*, vol. 43, pp. 1441-1441, November 2002.

[B55] S. A. Chkhenkeli, M. Sramka, G. S. Lortkipanidze, T. N. Rakviashvili, E. S. Bregvadze, G. E. Magalashvili, T. S. Gagoshidze, and I. S. Chkhenkeli, "Electrophysiological effects and clinical results of direct brain stimulation for intractable epilepsy," *Clinical Neurology And Neurosurgery*, vol. 106, pp. 318-329, September 2004.

[B56] J. O. Willoughby, "Mechanisms underlying partial (focal, or lesional) epilepsy," *Journal Of Clinical Neuroscience*, pp. 291-294, 2000.

[B57] H. Khosravani, R. Pinnegar, R. Mitchell, B. Bardakjian, P. Carlen, and P. Federico, "Increased high frequency oscillations precede in vitro low Mg2+seizures," *Epilepsia*, pp. 272-272, 2005.

[B58] V. I. Dzhala and K. J. Staley, "Mechanisms of fast ripples in the hippocarnpus," *Journal Of Neuroscience*, pp. 8896-8906, 2004.

[B59]. J. Gimsa, B. Habel, U. Schreiber, U. v. Rienen, U. Strauss, and U. Gimsa, "Choosing electrodes for deep brain stimulation experiments-electrochemical considerations," *Journal of Neuroscience Methods*, vol. 142, p. 251, 2005.

[B60] J. C. Williams, R. L. Rennaker, and D. R. Kipke, "Long-term neural recording characteristics of wire microelectrode arrays implanted in cerebral cortex," *Brain Research Protocols*, vol. 4, pp. 303-313, December 1999.

[B61] J. C. Sanchez, N. Alba, T. Nishida, C. Batich, and P. R. Carney, "Structural modifications in chronic microwire electrodes for cortical neuroprosthetics: a case study," *submitted to IEEE Transactions on Neural Systems and Rehabilitation Engineering*, 2005

[B62] A. M. Kuncel and W. M. Grill, "Selection of stimulus parameters for deep brain stimulation," *Clinical Neurophysiology*, vol. 115, pp. 2431-2441, 2004.

[B63] P. H. Gorman and J. T. Mortimer, "The effect of stimulus parameters on the recruitment characteristics of direct nerve stimulation," *IEEE Trans. Biomed. Eng.*, vol. 30, pp. 407-414, 1983.

[B64] W. M. Grill and J. T. Mortimer, "Stimulus waveforms for selective neural stimulation," *IEEE Eng. Med. Biol.*, vol. 14, pp. 375-385, 1995.

[B65] D. R. McNeal, "Analysis of a model for excitation of myelinated nerve," *IEEE Trans. Biomed. Eng.*, vol. 23, pp. 329-337, 1976.

[B66] D. H. Johnson, "Point Process Models of Single-Neuron Discharges," *Journal of Computational Neuroscience*, vol. 3, pp. 275-299, 1996.

[B67] A. Knoblauch and G. Palm, "What is Signal and What is Noise in the Brain?," *BioSystems*, vol. 79, pp. 83-90, 2005.

[B68] W. R. Softky and C. Koch, "The Highly Irregular Firing of Cortical Cells is Inconsistent with Temporal Integration of Random EPSPs," *The Journal of Neuroscience*, vol. 13, pp. 334-350, 1993.

[B69] J. C. Sanchez, Z. Liu, and P. R. Carney, "Identifying the Seizure Onset Zone using Amplitude Modulated Slow Potentials, Gamma, Fast Gamma, and Neural Ensemble Activity," in *60th Annual Meeting of the American Epilepsy Society*, San Diego, Calif., 2006.

[B70] J. C. Sanchez, P. R. Carney, and J. C. Principe, "Analysis of Amplitude Modulated Control Features for ECoG Neuroprosthetics" in *IEEE International Conference of the Engineering in Medicine and Biology Society*, New York, N.Y., 2006.

[B71] E. Patrick, M. Ordonez, N. Alba, J. C. Sanchez, and T. Nishida, "Design and Fabrication of a Flexible Substrate Microelectrode Array for Brain Machine Interfaces" in *IEEE International Conference of the Engineering in Medicine and Biology Society*, New York, N.Y., 2006.

The invention has been described in detail with reference to preferred embodiments thereof. However, it will be appreciated that those skilled in the art, upon consideration of this disclosure, may make modifications and improvements within the spirit and scope of the invention. It is understood that this invention is not limited to the particular materials and methods described herein. It is also to be understood that the terminology used herein is for the purpose of describing particular embodiments and is not intended to limit the scope of the present invention, which will be limited only by the appended claims.

What is claimed is:

1. A micro-control neuroprosthetic device for predicting and controlling epileptic neuronal activity, comprising:

a detection system that detects and collects electrophysiological information comprising action potentials of single or ensembles of neurons in a neural structure, wherein the neural structure is selected from the group consisting of the limbic system, hippocampus, entorhinal cortex, CA1, CA2, CA3, dentate, and hippocampal commissure;

a bandpass filter that filters the detected and collected electrophysiological information to select electrophysiological information having a frequency between 300 Hz and 6 kHz;

an analysis system that evaluates the filtered electrophysiological information and performs a real-time extraction of neuron firing features and from the extracted features determines when electrical stimulus intervention is required;

a stimulation intervention system that provides electrical stimulus output signals having a desired stimulation frequency and stimulation intensity directly to the neural structure being monitored and in which abnormal neuronal activity is detected; and wherein the analysis system further analyzes collected electrophysiological information following electrical stimulus intervention to assess the short-term effects of the stimulation intervention and to provide outputs to maintain or modify such stimulation intervention.

2. The micro-control neuroprosthetic device of claim 1, wherein the detection system comprises an array of a plurality of electrodes forming a multi-site array.

3. The micro-control neuroprosthetic device of claim 2, wherein the electrode array further includes a switching stage to selectively couple the array to a detector and to the stimulation intervention system.

4. The micro-control neuroprosthetic device of claim 3, wherein the electrode array is arranged so as to form a plurality of discrete channels and wherein the switching stage is operated by the stimulation intervention system so that output signals are directed to one or more of the plurality of channels in which it is determined that stimulation intervention is required.

5. A method for controlling epileptic neuronal activity, comprising the steps of:
monitoring a neural structure and detecting and collecting electrophysiological information comprising action potentials of single or ensembles of neurons in the neural structure being monitored, wherein the neural structure is selected from the group consisting of the limbic system, hippocampus, entorhinal cortex, CA1, CA2, CA3, dentate, and hippocampal commissure;
applying a bandpass filter to detected and collected electrophysiological information to select electrophysiological information having a frequency between 300 Hz and 6 kHz;
analyzing the filtered electrophysiological information;
performing a real-time extraction of neuron firing features;
determining from the real-time extraction of neuron firing features the onset of an epileptic state and of abnormal neural firing; and
providing electrical stimulation output signals having a desired stimulation frequency and stimulation intensity to at least a portion of a neural structure being monitored responsive to said determining, to control the epileptic neuronal activity.

6. The method of claim 5, wherein said performing a real-time extraction of neuron firing features from the filtered electrophysiological information comprises performing at least one analysis selected from the group consisting of coefficient of variation, spectral analysis, signal integration, signal energy, match filter, hidden Markov modeling, linear predictive modeling and non-linear predictive modeling (dynamical or feedforward).

7. The method of claim 6, wherein said performing a real-time extraction of neuron firing features from the filtered electrophysiological information comprises performing coefficient of variation analysis.

8. The method of claim 6, wherein said performing a real-time extraction of neuron firing features from the filtered electrophysiological information comprises performing spectral analysis.

9. The method of claim 6, wherein said performing a real-time extraction of neuron firing features from the filtered electrophysiological information comprises performing signal integration analysis.

10. The method of claim 6, wherein said performing a real-time extraction of neuron firing features from the filtered electrophysiological information comprises performing signal energy analysis.

11. The method of claim 6, wherein said performing a real-time extraction of neuron firing features from the filtered electrophysiological information comprises performing match filter analysis.

12. The method of claim 6, wherein said performing a real-time extraction of neuron firing features from the filtered electrophysiological information comprises performing hidden Markov modeling.

13. The method of claim 6, wherein said performing a real-time extraction of neuron firing features from the filtered electrophysiological information comprises performing linear predictive modeling.

14. The method of claim 6, wherein said performing a real-time extraction of neuron firing features from the filtered electrophysiological information comprises performing non-linear predictive modeling (dynamical or feedforward).

15. The method of claim 5, wherein said action potentials of single or ensembles of neurons in the neural structure are detected at sample frequencies between about 200 Hz and about 24 kHz.

16. The method of claim 5, further comprising the steps of:
collecting electrophysiological information during or following said providing stimulation output signals;
analyzing the collected information and assessing the short-term effects of the stimulation output signals on one of the onset of the epileptic state or abnormal neural firing;
determining if there is one of increased, decreased or maintenance of neuron/ensemble activity from said analyzing; and
maintaining or modifying the stimulation output signals being provided, based on the determined increased, decreased or maintenance of neuron/ensemble activity.

17. The method of claim 5, further comprising the steps of:
providing an electrode array being configured to selectively detect electrophysiological information comprising action potentials, and to output the electrical stimulation output signals;
wherein the electrode array being configured is configured so as to create a plurality of channels and wherein said providing electrical stimulation output signals includes providing electrical stimulation output signals having a desired stimulation frequency and stimulation intensity to one or more of the plurality of channels, in which in said one or more channels it is determined that there is one of the onset of an epileptic state or abnormal neuronal firing.

* * * * *